United States Patent [19]
Rothschild et al.

[11] Patent Number: 5,939,264
[45] Date of Patent: Aug. 17, 1999

[54] GENES AND GENETIC MARKERS FOR IMPROVED REPRODUCTIVE TRAITS IN ANIMALS

[75] Inventors: Max F. Rothschild; Christopher K. Tuggle, both of Ames, Iowa; Lori A. Messer, Lincoln, Nebr.; Tun-Ping Yu, Ames, Iowa

[73] Assignee: Iowa State University Research Foundation, Inc., Ames, Iowa

[21] Appl. No.: 08/896,365

[22] Filed: Jul. 18, 1997

Related U.S. Application Data

[60] Provisional application No. 60/022,180, Jul. 19, 1996.

[51] Int. Cl.$^6$ .............................. C12Q 1/68; C12P 19/34; C07H 21/02; C07H 21/04
[52] U.S. Cl. ........................... 435/6; 435/91.1; 435/94.2; 435/172.3; 536/23.1; 536/24.3; 536/24.31; 536/24.33
[58] Field of Search .............................. 435/6, 91.1, 91.2, 435/172.3; 536/22.1, 23.1, 24.3, 24.31, 24.32, 24.37

[56] References Cited

U.S. PATENT DOCUMENTS

| | | | |
|---|---|---|---|
| 5,260,432 | 11/1993 | Takaku et al. | 536/23.5 |
| 5,374,526 | 12/1994 | Rothschild et al. | |
| 5,550,024 | 8/1996 | Rothschild et al. | |

FOREIGN PATENT DOCUMENTS

| | | | |
|---|---|---|---|
| WO 95/35320 | 12/1995 | WIPO . | |
| WO 96/33288 | 10/1996 | WIPO | C12Q 1/68 |
| WO 96/41892 | 12/1996 | WIPO | C12Q 1/68 |

OTHER PUBLICATIONS

Ollivier et al, "The use of selection experiments for detecting quantitative trait loci", Genetic. Res. 69:227–232, Jun. 1997.

Messer et al, "Mapping and investigation of candidate genes for litter size in french large white pigs", Animal Sciences 27 (suppl. 2): 114, Dec. 1996.

Trout et al, "The retinol binding protein of the expanding pig blastocyts: molecular cloning and expression in trophoectoderm and embryonic disk", Mol. Endocrinol. 5(10):1533–40 Abstract Only, Oct. 1991.

Tsang et al, "Cloning and expression kinetics of porcine vascular cell adhesion molecule", Biochem. Biophys. Res. Comm. 201(2):805–812, Jun. 1994.

Edery, M., "Identification and sequence analysis of a second form of prolactin receptor by molecular cloning of complementary DNA from rabbit mammary gland", *Proc. Natl. Acad. Sci. USA*, 86:2112–2116 (1989).

Rothschild, et al., "The estrogen receptor locus is associated with a major gene influencing litter size in pigs", *Proc. Natl. Acad. Sci. USA* 93:201–205 (1996).

Sommer, R., "Minimal homology requirements for PCR primers", *Nucleic Acids Research*, 17(16) 6749 (1989).

Stratagene catalog (1995) pp. 131 and 161.

*Primary Examiner*—Jeffrey Fredman
*Attorney, Agent, or Firm*—Zarley, McKee, Thomte, Voorhees & Sease

[57] ABSTRACT

Disclosed herein are genetic markers for favorable reproductive traits in animals such as litter size, and weaning weight. Methods for identifying such markers, and methods of screening animals to determine those more likely to produce favorable reproductive traits and preferably selecting those animals for future breeding purposes. The markers are based upon the presence or absence of certain polymorphisms in the pig reproductive genes, including retinol binding protein 4, retinoic acid receptor gamma, melatonin receptor 1*a*, and vascular cell adhesion molecule 1

49 Claims, 12 Drawing Sheets

```
A1: AAATGCAGTG AACTCTTGGA AAGACATGGC TGCCTATGCC CTTGCGGTGT  50
A2: AAATGCAGTG AACTCTTGGA AAGACATGGC TGCCTATGCC CTTGCGGTGT  50
B : AAATGCAGTG AACTCTTGGA AAGACATGGC TGCCTATGCC CTTGCGGTGT  50
C : AAATGCAGTG AACTCTTGGA AAGACATGGC TGCCTATGCC CTTGCGGTGC  50

A1: GCACGAAGCC AAAGGAAAAC GGCTTTCTCA AAAATAGGCA CTACCCCTGA  100
A2: GCACGAAGCC AAAGGAAAAC GGCTTTCTCA AAAATAGGCA CTACCCCTGA  100
B : GCACGAAGCC AAAGGAAAAC GGCTTTCTCA AAAATAGGCA CTACCCCTGA  100
C : GCATGAAGCC AAAGGAAAAC GGCTTTCTCA AAAATAGGCA CTACCCCTGA  100

A1: GATATGGTGA CTGGGGTGGT GTCATGAAGT GTATGTACAA TAACGTGATT  150
A2: GATATGGTGA CTGGGGTGGT GTCATGAAGT GTATGTACAA TAACGTGATT  150
B : GATATGGTGA CTGGGGTGGT GTCATGAAGT GTATGTACAA TAACGTGATT  150
C : GATATAGTGA CTGGGGTGGT GTCATGAAGT GTATGTACAA TAATGTGATT  150

A1: TGTATATATG TAAAATAAAA TTATGCCATA GGAAGATCGC CTGGAATATC  200
A2: TGTATATATG TAAAATAAAA TTATGCCATA GGAAGATCGC CTGCAATATC  200
B : TGTATATATG TAAAATAAAA TTATGCCATA GGAAGATCGC CTGCAATATC  200
C : TGTATATATG TAAAATAAAA TTATGCCATA GGAAGATCTC CTGGAATATC  200

A1: AGCCCTCCAT AGTCACATTT CTAAAATTAT CA--GTTTG CTTGGACTGA  250
A2: AGCCCTCCAT AGTCACATTT CTAAAATTAT CA--GTTTG CTTGGACTGA  250
B : AGCCCTCCAT AGTCACATTT CTAAAATTAT CA--GTTTG CTTGGACTGA  250
C : AGCCCTCCAT AGTCACATTT CTAAAATTAT CAAAGTGTTG CTTGGACTGA  250

A1: TCGTTATAAC TTAATGCATC TTAATAT-GA CTGGCACTTT TTAATATTTT  300
A2: TCGTTATAAC TTAATGCATC TTAATAT-GA CTGGCACTTT TTAATATTTT  300
B : TCGTTATAAC TTAATGCATC TTAATAT-GA CTGGCACTTT TTAATATTTT  300
C : TCGTTATAAC TTAATGCATC TTAATATCGA CTGGCACTTT TTAATATTTT  300
                                 TaqI Polymorphic site A1: ATGTCATCTT TTTAATATTT TGTTACGACT TTTCAATATT TTATTCCTTT  350
A2: ATGTCATCTT TTTAATATTT TGTTACGACT TTTCAATATT TTATTCCTTT  350
B : ATGTCATCTT TTTAATATTT TGTTACGACT TTTCAATATT TTATTTCCTT  350
C : ATGTCATCTT TTTAATATTT TGTTATGACT TTTCAATATT TTATTTCCTT  350

A1: TAACAATATT TGATTCCTAT ACAGGTCATG GACAACAATT TCATGTTTTG  400
A2: TAACAATATT TGATTCCTAT ACAGGTCATG GACAACAATT TCATGTTTTG  400
B : TAACAATATT TGATTCCTAT AAAGGTCATG GACAACAATT TCATGTTTTG  400
C : TAACAATATT TGATTCCTAT AAAGGTCATG GACAACAATT TCATGTTTTG  400

A1: TAAAGATGCC AGGGTTTTAG ATTGTTACAG GCAAATGA-- -TAAACCAAG  450
A2: TAAAGATGCC AGGGTTTTAG ATTGTTACAG GCAAATGA-- -TAAACCAAG  450
B : TAAAGATGCC AGGGTTTTAG ATTGTTACAG GCAAATGA-- -TAAACCAAG  450
C : TAAAGATGCC AGGGTTTTAG ATTGTTACAG GCAAATAACA ATAAACCAAG  450

A1: AAAGAACTGG GTT  463
A2: AAAGAACTGG GTT  463
B : AAAGAACTGG GTT  463
C : AAAGAACTGG GTT  463
```

FIG.2

VCAM A1

AAATGCAGTG AACTCTTGGA AAGACATGGC TGCCTATGCC CTTGCGGTGT
GCACGAAGCC AAAGGAAAAC GGCTTTCTCA AAAATAGGCA CTACCCCTGA
GATATGGTGA CTGGGGTGGT GTCATGAAGT GTATGTACAA TAACGTGATT
TGTATATATG TAAAATAAAA TTATGCCATA GGAAGATCGC CTGGAATATC
AGCCCTCCAT AGTCACATTT CTAAAATTAT CAGTGTTGCT TGGACTGATC
GTTATAACTT AATGCATCTT AATATGACTG GCACTTTTA ATATTTATG
TCATCTTTTT AATATTTGT TACGACTTTT CAATATTTA TTCCTTTTAA
CAATATTTGA TTCCTATACA GGTCATGGAC AACAATTTCA TGTTTTGTAA
AGATGCCAGG GTTTTAGATT GTTACAGGCA AATGATAAAC CAAGAAAGAA
CTGGGTT

VCAM A2

AAATGCAGTG AACTCTTGGA AAGACATGGC TGCCTATGCC CTTGCGGTGT
GCACGAAGCC AAAGGAAAAC GGCTTTCTCA AAAATAGGCA CTACCCCTGA
GATATGGTGA CTGGGGTGGT GTCATGAAGT GTATGTACAA TAACGTGATT
TGTATATATG TAAAATAAAA TTATGCCATA GGAAGATCGC CTGCAATATC
AGCCCTCCAT AGTCACATTT CTAAAATTAT CAGTGTTGCT TGGACTGATC
GTTATAACTT AATGCATCTT AATATGACTG GCACTTTTA ATATTTATG
TCATCTTTTT AATATTTGT TACGACTTTT CAATATTTA TTCCTTTTAA
CAATATTTGA TTCCTATACA GGTCATGGAC AACAATTTCA TGTTTTGTAA
AGATGCCAGG GTTTTAGATT GTTACAGGCA AATGATAAAC CAAGAAAGAA
CTGGGTT

VCAM B

AAATGCAGTG AACTCTTGGA AAGACATGGC TGCCTATGCC CTTGCGGTGT
GCACGAAGCC AAAGGAAAAC GGCTTTCTCA AAAATAGGCA CTACCCCTGA
GATATGGTGA CTGGGGTGGT GTCATGAAGT GTATGTACAA TAACGTGATT
TGTATATATG TAAAATAAAA TTATGCCATA GGAAGATCGC CTGCAATATC
AGCCCTCCAT AGTCACATTT CTAAAATTAT CAGTGTTGCT TGGACTGATC
GTTATAACTT AATGCATCTT AATATGACTG GCACTTTTA ATATTTATG
TCATCTTTTT AATATTTGT TACGACTTTT CAATATTTA TTTCCTTTAA
CAATATTTGA TTCCTATAAA GGTCATGGAC AACAATTTCA TGTTTTGTAA
AGATGCCAGG GTTTTAGATT GTTACAGGCA AATGATAAAC CAAGAAAGAA
CTGGGTT

VCAM C

AAATGCAGTG AACTCTTGGA AAGACATGGC TGCCTATGCC CTTGCGGTGC
GCATGAAGCC AAAGGAAAAC GGCTTTCTCA AAAATAGGCA CTACCCCTGA
GATATAGTGA CTGGGGTGGT GTCATGAAGT GTATGTACAA TAATGTGATT
TGTATATATG TAAAATAAAA TTATGCCATA GGAAGATCTC CTGGAATATC
AGCCCTCCAT AGTCACATTT CTAAAATTAT CAAAGTGTTG CTTGGACTGA
TCGTTATAAC TTAATGCATC TTAATATCGA CTGGCACTTT TTAATATTTT
ATGTCATCTT TTTAATATTT TGTTATGACT TTTCAATATT TTATTTCCTT
TAACAATATT TGATTCCTAT AAAGGTCATG GACAACAATT TCATGTTTTG
TAAAGATGCC AGGGTTTTAG ATTGTTACAG GCAAATAACA ATAAACCAAG
AAAGAACTGG GTT

FIG. 3

Porcine embryo RAR gamma cDNA partial sequence (from PCR product)

5'.........AACTGAGCCCCCAGTTAGAAGAGCTCATCACCAAGGTCAGCAAAGTCCATCAAGAGACGCT
CCTCCCGCTCTGCCAGCTGGGCAATTACACCACGAACTCCAGTGTAGACCACCGTGTGCAGCTGGA
TCTGGGGCTGTGGGACCAAGTTCAGTGAGCTGGTCACCAAGTGCATCATTAAGATCGCGGAGNTTGT
CAAGCGGCTGTCCTGTTTTACAGGGCTCCAGTATTGCTGACCACTCTGCTCAAGGCTGCTGCCTG
CCTGGACATCCTGATGCTGCGGNTCTGCACCAAGGTCACGATGCACGATGCTGACTTCCCCACCCTC
TGATGGGCTGACCCTGAACCGGANCCAGATGCACCAGATGCTGGAGATGACACAGAGGCTCTCAGCCGC
CTGTGCCTTTGCTGGGCAGCTCCTGCCACTGGAGACCTGGAGGAACCCGAGTAAGTGGACAAGCTGCAGGAG
CATCTGCCTCATCTGCGGAGACCGCGATGGAGCCCTGAGGCTCTATG.........3'

FIG. 8

```
Hum1a  :       MQGNGSALPNASQPVLRGDGA---RPSWLASALACVLIFTIVVDILG    44
Sheep  :   1  MAGRLWGSPGGTPKGNGSSALLNVSQAAPGAGDGVRPRPSWLAATLASILIFTIVVDIVG    60

Hum1a  :  45  NLLVILSVYRNKKLRNAGNIFVVSLAVADLVVAIYPYPLVLMSIFNNGWNLGYLHCQVSG   104
Sheep  :  61  NLLVVLSVYRNKKLRNAGNVFVVSLAVADLLVAVYPYPLALASIVNNGWSLSSLHCQLSG   120
Cattle :                           YPLALASIVNDGWSLSSLHCQLSG    26

Hum1a  : 105  FLMGLSVIGSIFNITGIAINRYCYICHSLKYDKLYSSKNSLCYVLLIWLLTLAAVLPNLR   164
Sheep  : 121  FLMGLSVIGSVFSITGIAINRYCCICHSLRYGKLYSGTNSLCYVFLIWTLTVAIVPNLC   180
Cattle :  27  FLMGLSVIGSVFNITGIAINRYCCICHSLRYNKLYSSTNSLCYVFLIWMLTLVAIVPNLC    86
Pig    :                          YCYICHSLKYDRWYSNRNSLCCVFLICVLTLVAIVPNLC Hum1a  : 165  AGTLQYDPRIYSCTFAQSVSSAYTIAVVVFHFLVPMIIVIFCYLRIWILVLQVRQRVKPD   224
Sheep  : 181  VGTLQYDPRIYSCTFTQSVSSAYTIAVVVFHFIVPMLVVVFCYLRIWALVLQVRWKVKPD   240
Cattle :  87  VGTLQYDPRIYSCTFTQSVSSAYTIAVVVFHFIVPMLVVIFCYLRIWALVLQVRWRVKPD   146
Pig    :      MGTLQYDPRIYSCTFAQSVSSAYTIAVVVFHFLVPMVIVIFRYLRIWVLVLQIRWRAKPE Hum1a  : 225  RKPKLKPQDFRNFVTMFVVFVLFAICWAPLNFIGLAVASDPASMVPRIPEWLFVASYYMA   284
Sheep  : 241  NKPKLKPQDFRNFVTMFVVFVLFAICWAPLNFIGLVVASDPASMAPRIPEWLFVASYYMA   300
Cattle : 147  NKPKLKPQDFRNFVTMFVVFVLFAICWAPLNFIGLVVASEPASMAPRIPEWLFVASYYMG   206
Pig    :      NNPRLKPQDFRNFVTMFVVFVLFAICWAPLNFIGLAVASDPASMAPRIPEWLFV       153

Hum1a  : 285  YFNSCLNAIIYGLLNQNFRKEYRRIIVSLCTARVFFVDSSNDVADRVKWKPSPLMTNNNV   344
Sheep  : 301  YFNSCLNAIIYGLLNQNFRQEYRKIIVSLCTTKMFFVDSSNHVADRIKRKPSPLIANHNL   360
Cattle : 207  YFNSCLNAIIYGLLNQNFRQEYRKIIVSLCTTKMFFVDSSNHVAHRIKRKPSP         257

Hum1a  : 345  VKVDSV   350
Sheep  : 361  IKVDSV   366
```

FIG. 9

GENES AND GENETIC MARKERS FOR IMPROVED REPRODUCTIVE TRAITS IN ANIMALS

CROSS REFERENCE TO RELATED APPLICATION

This application claims benefit of U.S. provisional application Ser. No. 60/022,180 filed Jul. 19, 1996, entitled DNA POLYMORPHISMS IN GENES THAT ARE USEFUL FOR TESTING AND SELECTING FOR INCREASED LITTER SIZE IN PIGS.

FIELD OF THE INVENTION

This invention relates generally to the detection of genetic differences for reproductive efficiency among animals. More particularly the invention relates to genetic markers which have been identified in several genes indicative of heritable phenotypes associated with improved reproductive traits. Methods and compositions for use of these markers in genotyping of animals and selection are also disclosed.

BACKGROUND OF THE INVENTION

Reproductive efficiency, particularly as it relates to litter size, is the major limiting factor in the efficient production of pork as well as most other livestock animals. Genetic variability exists for several reproductive measures. Average litter size among breeds pigs varies from 4–16 pigs per litter. Mean age at puberty varies from 3 to 7 months of age. This genetic variability within breeds suggests that genetic improvement in reproduction is possible. The number of pigs born alive in the United States averages approximately 9.5 pigs per litter. Heritability for litter size is low (10%–15%), and standard genetic methods of selecting breeding females on the basis of past litter size have not been effective. Therefore, there is a need for an approach that deals with selection for reproductive traits at the cellular or DNA level.

Chinese breeds are known for reaching puberty at an early age and for their large litter size. American breeds are known for their greater growth rates and leanness. Thus, it would be desirable to combine the best characteristics of both types of breeds, thereby improving the efficiency of U.S. pork production. These efforts would be greatly assisted by the discovery of genes or genetic markers that are associated with improved reproductive traits such as increased litter size in pigs.

RFLP analysis has been used by several groups to study pig DNA. Jung et al., *Theor. Appl. Genet.*, 77:271–274 (1989), incorporated herein by reference, discloses the use of RFLP techniques to show genetic variability between two pig breeds. Polymorphism was demonstrated for swine leukocyte antigen (SLA) Class I genes in these breeds. Hoganson et al., Abstract for Annual Meeting of Midwestern Section of the American Society of Animal Science, Mar. 26–28, 1990, incorporated herein by reference, reports on the polymorphism of swine major histocompatibility complex (MHC) genes for Chinese pigs, also demonstrated by RFLP analysis. Jung et al. *Animal Genetics*, 26:79–91 (1989), incorporated herein by reference, reports on RFLP analysis of SLA Class I genes in certain boars. The authors state that the results suggest that there may be an association between swine SLA/MHC Class I genes and production and performance traits. They further state that the use of SLA Class I restriction fragments, as genetic markers, may have potential in the future for improving pig growth performance.

Further, U.S. Pat. No. 5,550,024 to Rothschild et al. discloses a polymorphism in the pig estrogen receptor gene which is associated with larger litter size, the disclosure of which is incorporated herein by reference.

Another pig hormone related to beneficial reproductive traits is Prolactin. Prolactin (PRL) is an anterior pituitary peptide hormone involved in many different endocrine activities, but is essential for reproductive success. Use of polymorphic loci in the prolactin receptor gene as markers for increased litter size is described and disclosed in U.S. patent application Ser. No. 08/812,208, the disclosure of which is hereby incorporated by reference.

The present invention provides genetic markers, based upon the discovery of polymorphisms in reproductive genes, which relate to improved reproductive traits such as testicular size, sperm volume, concentration of sperm, sperm quality, libido and breeding aggressiveness for males. For females reproductive traits include litter size, number born alive, litter birth weight, number weaned, age at puberty, weaning to oestrus, farrowing interval, ovulation rate, uterine capacity and embryo survival in pigs. This will permit genetic typing of pigs for their reproductive genes and for determination of the relationship of specific genes and markers to reproductive traits. It will also permit the identification of individual males and females that carry beneficial genotypes. In the case of females it would permit that a female would be expected to produce a litter size larger than the average earlier than average or healthier than average for their breed, or in the case of males, for their female offspring to have the beneficial traits. Thus, the markers will be selection tools in breeding programs to develop lines and breeds that produce litters with favorable reproductive phenotypes.

It is an object of the invention to provide a method of screening pigs to determine those more likely to produce larger litters.

Another object of the invention is to provide a method for identifying genetic markers for reproductive traits such as pig litter size.

A further object of the invention is to provide genetic markers for pig litter size.

Yet another object of the invention is to provide a kit for evaluating a sample of pig DNA for specific genetic markers associated with favorable reproductive traits.

Additional objects and advantages of the invention will be set forth in part in the description that follows, and in part will be obvious from the description, or may be learned by the practice of the invention. The objects and advantages of the invention will be attained by means of the instrumentality's and combinations particularly pointed out in the appended claims.

SUMMARY OF THE INVENTION

To achieve the objects and in accordance with the purpose of the invention, as embodied and broadly described herein, the present invention provides a method for screening pigs and other animals to determine those more likely to have beneficial reproductive phenotypes such as a larger litter, when bred or to select against pigs which have alleles indicating unfavorable phenotypes.

As used herein "larger litters" means a significant increase in litter size above the mean of a given population.

As used herein the term "reproductive trait" shall include any trait which is indicative of improved reproduction efficiency including but not limited to testicular size, sperm volume, sperm concentration, sperm quality, libido, breeding aggressiveness, litter size, number born alive, litter birth weight, number weaned, age at puberty, weaning to oestrus interval, farrowing interval, ovulation rate, uterine capacity, and embryo survival.

As used herein the term "reproductive gene" shall mean any gene which encodes a gene product which, upon expression, influences either favorably or negatively a reproductive trait. Examples of such genes include but are not limited to the estrogen receptor gene, the prolactin receptor gene and other genes disclosed and described herein.

Thus, the present invention provides a method for screening pigs to determine those more likely to produce beneficial reproductive traits such as larger litters, and/or those less likely to produce smaller litters, which method comprises the steps 1) obtaining a sample of genomic DNA from a pig or other animal; and 2) analyzing the genomic DNA obtained in 1) to determine which allele(s) is/are present. Briefly, the sample of genetic material is obtained and is analyzed to determine the presence or absence of a polymorphism in a gene that is correlated with a desirable reproductive trait.

In a preferred embodiment the polymorphism is a restriction fragment length polymorphism and the assay comprises identifying the reproductive gene from isolated genetic material; exposing the gene to a restriction enzyme that yields restriction fragments of the gene of varying length; separating the restriction fragments to form a restriction pattern, such as by electrophoresis or HPLC separation; and comparing the resulting restriction fragment pattern from an animal reproductive gene that is either known to have or not to have the desired marker. If an animal tests positive for the marker, such animal can be considered for inclusion in the breeding program. If the animal does not test positive for the marker genotype the animal can be culled from the group and otherwise used.

In a most preferred embodiment the gene of a fragment thereof is isolated by the use of primers and DNA polymerase to amplify a specific region of the gene which contains the polymorphism. Next the amplified region is either directly separated or sequenced or is digested with a restriction enzyme and fragments are again separated. Visualization of the separated fragments or RFLP pattern is by simple staining of the fragments, or by labeling the primers or the nucleoside triphosphates used in amplification.

In another embodiment, the invention comprises a method for identifying a genetic marker for reproductive traits such as litter size in a particular population. Male and female animals of the same breed or breed cross or similar genetic lineage are bred, and the number of offspring produced by each female is determined. A polymorphism in the reproductive gene of each animal is identified and associated with the desired reproductive trait. Preferably, PCR-RFLP analysis is used to determine the polymorphism.

It is also possible to establish linkage between specific alleles of alternative DNA markers and alleles of DNA markers known to be associated with a particular gene (e.g. the reproductive genes discussed herein), which have previously been shown to be associated with a particular trait. Thus, in the present situation, taking a particular reproductive gene, it would be possible, at least in the short term, to select for pigs or other animals likely to produce larger litters, or alternatively against pigs likely to produce smaller litters, indirectly, by selecting for certain alleles of a particular reproductive gene associated marker through the selection of specific alleles of alternative chromosome markers. For example markers known to be linked to prolactin receptor gene on porcine chromosome 16 includes SW1305, S0077, S0006, SW2411, SW1035 and S0111, which are all microsatellites, markers and Growth Hormone Receptor (GHR).

The invention further comprises a kit for evaluating a sample of DNA for the presence in genetic material of a desired genetic marker located in the reproductive gene indicative of the inheritable reproductive trait such as large litter size. At a minimum, the kit is a container with one or more reagents that identify a polymorphism in a reproductive gene. Preferably, the reagent is a set of oligonucleotide primers capable of amplifying a fragment of the selected reproductive gene that contains a polymorphism. Preferably, the kit further contains a restriction enzyme that cleaves the reproductive gene in at least one place, allowing for separation of fragments and detection of polymorphic loci.

The accompanying figures, which are incorporated herein and which constitute a part of this specification, illustrate one embodiment of the invention and, together with the description, serve to explain the principles of the invention.

DESCRIPTION OF THE FIGURES

FIG. 2 is a sequence comparison across A1(SEQ ID NO: 1), A2 (SEQ ID NO: 2), B (SEQ ID NO: 3) and C (SEQ ID NO: 4) alleles (italic fonts indicate point mutations. Primers used for genotyping are underlined.

FIG. 3 depicts individual VCAM1 allele sequence files (SEQ ID NO: 4).

FIG. 8 is the amplified gene product of porcine embryo RARG cDNA (SEQ ID NO: 5).

FIG. 9 is a comparison of the deduced amino acid sequence of melatonin receptors in human (SEQ ID NO: 6), sheep (SEQ ID NO: 7), cattle (SEQ ID NO: 8) and pig (SEQ ID NO: 10). The complete coding sequence of human melatonin receptor 1a (U14108) and sheep melatonin receptor (U14109) are shown. Pig sequence generated by primers MR5 and MR3 (double underlined) is provided. Sheep primers SMR5 and SMR3 are underlined.

DETAILED DESCRIPTION OF THE INVENTION

Figure 1:
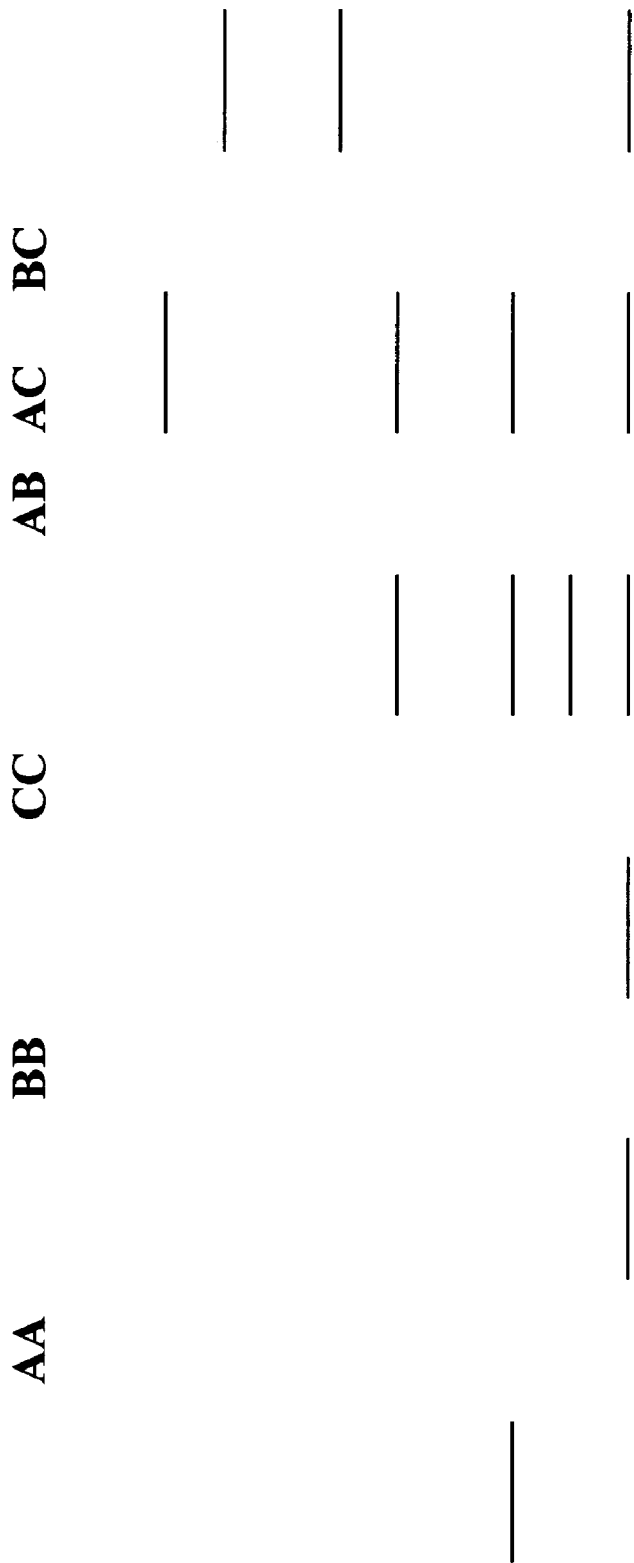
FIG. 1 depicts a schematic diagram of fragments seen by polyacrylamide gel electrophoresis of undigested VCAM1 PCR products.

Reference will now be made in detail to the presently preferred embodiments of the invention, which together with the following examples, serve to explain the principles of the invention.

The invention relates to genetic markers for beneficial reproductive traits such as litteranimals. It provides a meanimals. It provides a method of screening animals to determine those more likely to produce earlier, healthier, or larger litters when bred by identifying the presence or an absence of a polymorphism in certain reproductive genes that are correlated with these reproductive traits.

Thus, the invention relates to genetic markers and methods of identifying those markers in a pig or other animal of a particular breed, strain, population, or group, whereby the female is more likely to produce a litter that is significantly larger (number) is healthier, is earlier to mature, etc. above the mean for that particular breed, strain, population, or group. Any method of identifying the presence or absence of this marker may be used, including for example single-strand conformation polymorphism (SSCP) analysis, RFLP analysis, heteroduplex analysis, denaturing gradient gel electrophoresis, and temperature gradient electrophoresis, ligase chain reaction or even direct sequencing of the reproductive gene and examination for the certain recognition patterns.

Other possible techniques include non-gel systems such as TaqMan™ (Perkin Elmer). In this system oligonucleotide PCR primers are designed that flank the mutation in question and allow PCR amplification of the region. A third oligonucleotide probe is then designed to hybridize to the region containing the base subject to change between different alleles of the gene. This probe is labeled with fluorescent dyes at both the 5' and 3' ends. These dyes are chosen such that while in this proximity to each other the fluorescence of one of them is quenched by the other and cannot be detected. Extension by Taq DNA polymerase from the PCR primer positioned 5' on the template relative to the probe leads to the cleavage of the dye attached to the 5' end of the annealed probe through the 5' nuclease activity of the Taq DNA polymerase. This removes the quenching effect allowing detection of the fluorescence from the dye at the 3' end of the probe. The discrimination between different DNA sequences arises through the fact that if the hybridization of the probe to the template molecule is not complete, i.e. there is a mismatch of some form, the cleavage of the dye does not take place. Thus only if the nucleotide sequence of the oligonucleotide probe is completely complementary to the template molecule to which it is bound will quenching be removed. A reaction mix can contain two different probe sequences each designed against different alleles that might be present thus allowing the detection of both alleles in one reaction.

The use of RFLPs is the preferred method of detecting the polymorphism most preferred PCR-RFLP analysis. However, since the use of RFLP analysis depends ultimately on polymorphisms and DNA restriction sites along the nucleic acid molecule, other methods of detecting the polymorphisms can also be used. Such methods include ones that analyze the polymorphic gene product and detect polymorphisms by detecting the resulting differences in the gene product.

RFLP analysis in general is a technique well-known to those skilled in the art. See, for example, U.S. Pat. Nos. 4,582,788 issued Apr. 15, 1986 to Erlich and 4,666,828 issued May 19, 1987 to Gusella, 4,772,549 issued Sep. 20, 1988 to Frossard, and 4,861,708 issued Aug. 29, 1989 to Frossard, the disclosures of which are incorporated herein by reference. Broadly speaking, the technique involves obtaining the DNA to be studied, digesting the DNA with restriction endonucleases, separating the resulting fragments, and detecting the fragments of various genes.

In the present invention, a sample of genetic material is obtained from an animal. Samples can be obtained from blood, tissue, semen, etc. Generally, peripheral blood cells are used as the source, and the genetic material is DNA. A sufficient amount of cells are obtained to provide a sufficient amount of DNA for analysis. This amount will be known or readily determinable by those skilled in the art as explained in the material incorporated herein. The DNA is isolated from the blood cells by techniques known to those skilled in the art.

Next the region containing the polymorphism is amplified by the use of primers and standard techniques, such as the polymerase chain reaction. This technique is described in U.S. Pat. Nos. 4,683,195, issued Jul. 28, 1987 to Mullis et al., 4,683,202, issued Jul. 28, 1987 to Mullis, 4,800,159 issued Jan. 24, 1989 to Mullis, et al., 4,889,818 issued Dec. 26, 1989 to Gelfand, et al., and 4,902,624, issued Feb. 20, 1990 to Clumbus, et al., all of which are incorporated herein by reference. The selection of primers is discussed in the references mentioned and incorporated herein. The primers should amplify the region containing the polymorphism. Several primers for specific polymorphisms are disclosed herein. Other such primers are designable by those of skill in the art combined with the teachings herein, and are intended to be encompassed by the invention.

The isolated DNA is then analyzed and optionally digested with a restriction endonuclease that cleaves or cuts DNA hydrolytically at a specific nucleotide sequence, called a restriction site. Such endonucleases, also called restriction enzymes, are well-known to those skilled in the art. For the present invention, one should be chosen that cleaves the selected reproductive gene in at least one place, producing at least two fragments of the gene. A determination is made as to whether or not any such fragments are polymorphic and if any polymorphism (RFLP) is associated with a desired reproductive trait such as litter size by techniques known in the art in conjunction with the teachings contained herein. The amount of such enzyme to be added to the sample containing the pig DNA and the other appropriate conditions for treating the sample will be readily determinable to persons skilled in the art, given the teachings contained herein.

The restriction fragments are then analyzed by known techniques that generally involve either the separation of the fragments and visualization by staining or subsequent blotting and hybridization to obtain a particular pattern or the determination of different sizes of the fragments. The latter permits the identification of one or more fragments (markers) for increased litter size. The preferred separation technique is gel electrophoresis.

In this technique, the digested fragments are separated in a supporting medium by size under the influence of an applied electric field. Gel sheets or slabs, such as agarose or agarose-acrylamide, are typically used as the supporting medium. The sample, which contains the restriction fragments, is added to one end of the gel. One or more size markers are run on the same gel as controls to permit an estimation of the size of the restriction fragments. This procedure generally permits a degree of resolution that separates fragments that differ in size from one another by as little as 100 base pairs.

In alternative embodiments, the fragments are denatured and transferred physically from the gel onto a solid support, preferably a nylon membrane, by contacting the gel with the filter in the presence of appropriate reagents and under appropriate conditions that promote the transfer of the DNA. Such reagents and conditions are well-known to those skilled in the art. Thus, the relative positions of the DNA fragments resulting from the separation procedure are maintained.

The next step involves the detection of the various categories of sizes of the fragments or, alternatively, the detection of a fragment of a particular size. The latter may be of particular interest because it is a genetic marker associated with a desired reproductive trait. This is preferably accomplished via staining of the fragments with ethidium bromide or the like.

An alternative technique is the use of a hybridization probe. Such a probe is an oligonucleotidethr polynucleotide that is sufficiently complementary or homologous to the fragments to hybridize with them, forming probe-fragment complexes. Preferably, the probe is a CDNA probe. The oligonucleotide or polynucleotide is labeled with a detectable entity. This permits the detection of the restriction fragments, to which the probes are hybridized. The probes are labeled by standard labeling techniques, such as with a radiolabel, enzyme label, fluorescent label, biotin-avidin label, and the like. See U.S. Pat. Nos. 4,711,955 issued Dec. 8, 1987 to Ward et al. and 4,868,103 issued Sep. 19, 1989 to Stavrianopoulos et al., both of which are incorporated herein by reference.

The probes are contacted with the nylon membrane that contains the restriction fragments for a sufficient period of time and under appropriate hybridizing conditions for the probes to hybridize to the fragments. The filter is then preferably washed to remove unbound probes and other unwanted materials.

The probe-fragment complexes, which are bound to the filter, are then detected by known techniques. For example, if the probe has been radioactively labeled ($^{32}$P), detection involves contacting the nylon membrane paper with a piece of radiosensitive film. Following an appropriate exposure period, the fragments of interest, including control fragments, are visualized.

The detection step provides a pattern, resulting from the separation of the fragments by size. Comparison of these fragments with control fragments of known size that have also been run on the same gel permits the estimation of the size of the various groups of fragments. The various polymorphisms in the reproductive genes are then determined by comparison of the patterns produced by similar analysis of DNA from a number of different pigs. For some of the individual animals, the patterns will differ from the usual pattern produced by most of the other animals. This will be due to one or more restriction fragment length polymorphisms, i.e., restriction fragments of a different length produced by the endonuclease that cuts the reproductive gene. This indicates different base pair sequences in such pigs.

Once a particular RFLP has been identified, i.e., a restriction fragment of a particular length, a probe to this fragment may be constructed by the use of known techniques. This permits alternative and faster formats for detecting such polymorphism. For example, once the DNA is digested, a sandwich hybridization format can be used. Such an assay is disclosed in U.S. Pat. Nos. 4,486,539 issued December 4, 1984 to Ranki, et al., and 4,563,419 issued Jan. 7, 1986 to Ranki, et al., both of which are incorporated herein by reference. The sample is brought into contact with a capture probe that is immobilized on a solid carrier. The probe binds the fragment. The carrier is then washed, and a labeled detection probe is added. After additional washing, the detection probe is detected, thereby demonstrating the presence of the desired fragment.

In yet another embodiment, once the RFLP pattern has been determined or a particular polymorphic fragment has been determined, it is compared to a second, known RFLP pattern or fragment that is correlated with increased litter size. This second pattern or fragment has also been determined from the reproductive gene, using the same restriction endonuclease as the first and the same probe or an equivalent thereof under the same conditions.

In an alternative embodiment of the invention, the restriction fragments can be detected by solution hybridization. In this technique, the fragments are first hybridized with the probe and then separated. The separated probe-fragment complexes are then detected as discussed above. Generally, such complexes are detected on the gel without transfer to filter paper.

In a most preferred embodiment the polymorphism is detected by PCR amplification without any probe. This procedure is known to those of skill in the art and is disclosed in U.S. Pat. No. 4,795,699 entitled "DNA Polymerase" and U.S. Pat. No. 4,965,188 "Process for Amplifying, Detecting, and/or Cloning Nucleic Sequences Using a Thermostable Enzyme" both of which are incorporated herein by reference.

For this procedure primers are constructed to amplify the region in which the polymorphism lies. Accordingly primers which are preferably 4–30 bases are designed based upon the sequence surrounding the polymorphism including a forward 5', primer and a reverse or anti-sense primer 3' of the polymorphism. The primers need not be the exact complement, and substantially equivalent sequences are also acceptable. A DNA polymerase is then added such as Taq polymerase (many such polymerases are known and commercially available) in the presence of the four nucleoside triphosphates and often a buffering agent. Detection is facilitated by simple staining, such as with ethidium bromide, of separated products to detect for predicted sizes based upon the length of the region amplified. Reaction times, reagents, and design of primers are all known to those of skill in the art and are discussed in the patents incorporated herein by reference. Further PCR amplification may be used in combination with Single Strand Confirmation Polymorphism (SSCP). See Detection of Polymorphism, of Human DNA by Gel Electrophoresis as Single-Strand Conformation Polymorphisms, Orita et al, PNAS 86(8) April 1989 (2766–70); and Lessa-et al. Mol Ecol 2(2) p. 119–29 April 1993 "Screening Techniques for Detecting Allelic variation in DNA Sequences" which are incorporated by reference.

Although the methods described herein may be in terms of the use of a single restriction enzyme and a single set of primers, the methods are not so limited. One or more additional restriction enzymes and/or probes and/or primers can be used, if desired. Additional enzymes, constructed probes and primers can be determined through routine experimentation, combined with the teachings provided and incorporated herein.

Genetic markers for reproductive genes are determined as follows. Male and female animals of the same breed or breed cross or derived from similar genetic lineages are mated. The number of offspring with the beneficial reproductive trait is determined. For litter size the number of offspring produced by each female is determined. RFLP analysis of the parental DNA is conducted as discussed above in order to determine polymorphisms in the selected reproductive gene of each animal. The polymorphisms are associated with the traits. At least 20 and preferably at least 40 females are used in making these determinations. The number of times each female produces a litter (i.e., the parity) is at least 1 time. Preferably, the cycle of breeding and giving birth is repeated at least 2 times and most preferably 3 times.

When this analysis is conducted and the polymorphism is determined by RFLP or other analysis amplification primers may be designed using analogous human or other closely related animal known sequences. The sequences of many of the reproductive genes have high homology. Primers may also be designed using known gene sequences as exemplified in Genbank or even designed from sequences obtained from linkage data from closely surrounding genes. According to the invention sets of primers have been selected which identify regions in polymorphic reproductive genes. The polymorphic fragments have been shown to be alleles, and each was shown to be associated with beneficial reproductive traits, such as increased litter size, for various breeds. Often genotype associated with this trait alternates for different breeds. This outcome is similar to the situation disclosed in U.S. Pat. No. 5,374,523 entitled "Allelic variants of Bovine Somatotropin gene: Genetic marker for Superior Milk Production in Bovine" where the inventor found an allelic polymorphism is the somatotropin gene and one allelic form was beneficial for jersey cows and the alternate form was beneficial for Holstein cows.

The reagents suitable for applying the methods of the invention may be packaged into convenient kits. The kits provide the necessary materials, packaged into suitable containers. At a minimum, the kit contains a reagent that identifies a polymorphism in the selected reproductive gene that is associated with a reproductive trait such as increased litter size. Preferably, the reagent is a PCR set (a set of primers, DNA polymerase and 4 nucleoside triphosphates) that hybridize with the reproductive gene or a fragment thereof. Preferably, the PCR set and a restriction enzyme that cleaves the reproductive gene in at least one place are included in the kit. Preferably, the kit further comprises additional means, such as reagents, for detecting or measuring the detectable entity or providing a control. Other reagents used for hybridization, prehybridization, DNA extraction, visualization etc. may also be included, if desired.

The methods and materials of the invention may also be used more generally to evaluate animal DNA, genetically type individual animals, and detect genetic differences in animals. In particular, a sample of genomic DNA may be evaluated by reference to one or more controls to determine if a polymorphism in the reproductive gene is present. Preferably, RFLP analysis is performed with respect to the reproductive gene, and the results are compared with a control. The control is the result of a RFLP analysis of the reproductive gene of a different animal where the polymorphism of the reproductive gene is known. Similarly, the reproductive genotype of an animal may be determined by obtaining a sample of its genomic DNA, conducting RFLP analysis of the reproductive gene in the DNA, and comparing the results with a control. Again, the control is the result of RFLP analysis of the reproductive gene of a different animal. The results genetically type the pig by specifying the polymorphism in its selected reproductive gene. Finally, genetic differences among animals can be detected by obtaining samples of the genomic DNA from at least two animals, identifying the presence or absence of a polymorphism in the reproductive gene, and comparing the results.

These assays are useful for identifying the genetic markers relating to litter size, as discussed above, for identifying other polymorphisms in the reproductive gene that may be correlated with other characteristics, and for the general scientific analysis of genotypes and phenotypes.

The genetic markers, methods, and kits of the invention are also useful in a breeding program to improve litter size in a breed, line, or population of animals. Continuous selection and breeding of animals that are at least heterozygous and preferably homozygous for a polymorphism associated with a beneficial reproductive trait such as increased litter size would lead to a breed, line, or population having higher numbers of offspring in each litter of the females of this breed or line. Thus, the markers are selection tools.

The examples and methods herein disclose certain reproductive genes which have been identified to have a polymorphism which is associated either positively or negatively with a beneficial reproductive trait that will have an effect on reproductive efficiency of that animal. The identification of the existence of a polymorphism within a gene is often made by a single base alternative that results in a restriction site in certain allelic forms. A certain allele, however, as demonstrated and discussed herein may have a number of base changes associated with it that could be assayed for which are indicative of the same polymorphism. Further, other genetic markers or genes may be linked to the polymorphisms disclosed herein so that assays may involve identification of other genes or gene fragments but which ultimately rely upon genetic characterization of animals for the same polymorphism. Any assay which sorts and identifies animals based upon the allelic differences disclosed herein are intended to be included within the scope of this invention. One of skill in the art, once a polymorphism has been identified and a correlation to a particular trait proven, will understand that there are an infinite number of ways to genotype animals for this polymorphism. The design of these such alternative tests merely represent optimization of parameters known to those of skill in the art and are intended to be within the scope of this invention as fully described herein.

One reproductive gene which has been identified to have a polymorphic loci is vascular cell adhesion molecule 1. (VCAM1). VCAM1 was originally identified as a protein induced in the endothelium of blood vessels at sites of inflammation. Thus VCAM1 has traditionally been postulated to be a valuable marker for disease resistance and the inflammatory immune response. However, VCAM1 has also been shown to be expressed during the earliest stage of umbilical blood vessel development. In fact, VCAM1 is required for early vascular connection between the embryo and extra-embryonic membranes which later form the placenta. Without VCAM1 protein, neither the pre-umbilical structure called the allantois nor any placental blood vessels will form. VCAM1 is also expressed in the other critical part of the early circulatory system, the heart myocardium. A critical element controlling embryo survival and fetal growth rate is an adequate blood flow through the placenta.

According to the invention, applicants have identified a polymorphism within the VCAM1 reproductive gene which is associated with large litter size. This PCR-based polymorphism segregates in the PiGMaP reference families, where the Meishan and Large White each had breed-specific alleles (A=Meishan and B=Large White). Applicants have discovered that different alleles of this gene are correlated with increased litter size. The porcine VCAM1 cDNA has been sequenced and is available on Genbank, (Yvonne T.M. Tsang). The published Tsang sequence is the same as the allele B sequence disclosed herein. Other polymorphic loci have been identified in the VCAM1 gene, however, none have discovered one with a correlation to litter size. Helm et al. have discovered another polymorphism in the VCAM1 gene which is unrelated to that described and disclosed herein. Helm J. M., C. B. Schmitz, C. K. Tuggle, and M. F. Rothschild, 1994, "SacI restriction length polymorphism in a porcine vascular cellular adhesion molecule (VCAM1) gene", J. Anim. Sci. 72:2764.

VAMC1 maps in humans to HSA1, between two conserved syntenic groups found on SSC4 and SSC6. The teachings herein thus place VCAM1 within the syntenic group on SSC4. VCAM1 has been mapped to SSC4, which is interesting since a more proximal gene on human chromosome 1 (UOX, which maps between VCAM1 and TSHB in humans) has been mapped to pig chromosome 6, indicating the gene order has been scrambled between human 1 and pig 4/pig 6. Also, VAMC1 maps within a 22 cM gap, exactly between two microsatellite markers on the SSC4 map. This improves the marker coverage of this important chromosome, where major quantitative trait loci have been discovered (Andersson et al. 1994, Science 263:1771).

Other polymorphic reproductive genes which have been identified according to the invention include retinoic acid receptor gamma (RARG) and retinol binding protein 4 (RBP4).

Retinoic acid receptors (RARs) are ligand-inducible transcription factors. RAR subtypes are highly conserved across species and are differentially expressed during blastocyst elongation, a time when high embryo mortality occurs. Retinol-binding protein 4 (RBP4) is also expressed during elongation and has been postulated to transport and regulate the amount of retinol received by the fetuses. According to the invention polymorphisms have been identified and RARG and RBP4 have been mapped. A 795-bp RAR-gamma (RARG) cDNA fragment and a 311-bp RBP4 fragment were amplified from day 12 porcine blastocysts by RT-PCR and were radiolabeled for use in Southern blotting and RFLP analysis of digested genomic DNA of PiGMaP reference families. Hybridization of StuI digests with the RARG probe revealed a polymorphism with two alleles. An additional SacI polymorphism with two alleles was also found. The two-point linkage analysis of the SacI fragments found significant linkages between RARG and several loci on pig chromosome 5. The SacI digests hybridized with RBP4 revealed a polymorphism with two alleles and the linkage analysis found significant linkages with several loci on pig chromosome 14.

Yet another reproductive gene with alternate allelic forms according to the invention includes the melatonin receptor 1a gene(MTNR1A).

The hormone melatonin is secreted by the pineal gland and known to help regulate circadian rhythms and reproduction changes in seasonally reproductive mammals. These effects are exerted through the binding of melatonin to high affinity, G-protein-coupled receptors. The circadian effects are thought to be regulated by receptors in the hypothalamic suprachiasmatic nucleus, which is also the site of the biological clock (Klein et al. 1991). Receptors concentrated in the hypophyseal pars terberalis, the only common site with a high concentration of these receptors in seasonally breeding mammals, are thought to regulate reproductive effects of melatonin (Weaver et al. 1991). The cloning of the cDNA for a high affinity melatonin receptor in Xenopus laevis (Ebisawa et al. 1994) led to the cloning of melatonin receptor 1A (MTNR1A) in human and sheep (Reppert et al. 1994), though the gene was not mapped in sheep. The coding region of this gene is comprised of two exons separated by one large intron. The published comparison of the full-length coding regions of Xenopus, sheep and human MTNR1A sequences show regions of high sequence conservation (Reppert et al. 1994), and therefore a strong likelihood of conservation in other mammalian species.

It is to be understood that the application of the teachings of the present invention to a specific problem or environment will be within the capabilities of one having ordinary skill in the art in light of the teachings contained herein. The examples of the products and processes of the present invention appear in the following examples which are not intended to limit the scope or teachings of the invention.

EXAMPLE 1 (VCAM1)

A test was designed to follow VCAM1 alleles in specific populations and reference families to map the VAMC1 gene in the pig and determine the effect of VAMC1 genotypes on specific maternal reproductive traits.

Allelic differences at VCAM1

Three alleles were identified at pig VCAM1 using a PCR-based test in the 3' untranslated region of the gene, and five of the six possible genotypes possible in Pig Improvement Co. (PIC) line 19 were identified (see FIG. 1). Primers for the PCR test were designed from sequence determined herein and from a published sequence of pig VCAM1. A small population study (Table 1) shows that the major allele in commercial breed type animals is B, although C is also present.

TABLE 1

VCAM1 Allelic Frequency in Specific Breeds

| BREED | A | B | C |
|---|---|---|---|
| Duroc (17[1]) | 0.00 | 0.65 | 0.35 |
| Landrace (10) | 0.25 | 0.65 | 0.10 |
| Large White (12) | 0.00 | 1.00 | 0.00 |
| Meishan (12) | 1.00 | 0.00 | 0.00 |
| Wild Boar (2) | 0.00 | 0.75 | 0.25 |

[1]The number of animals in each breed

Allele A is seen only in Landrace and Meishan, where it is monomorphic in 12 animals surveyed. The alleles and genotypes are distinct based on gel mobility's of uncut DNA fragments (likely to be conformation polymorphisms) and/or restriction polymorphisms (i.e., TaqI site distinguishes alleles B and C). All three alleles have been sequenced in this region, and show sequence differences (FIGS. 2 and 3). In fact, additional sequence differences between putative similar A alleles from different AA genotype animals were discovered, and have designated these alleles as $A_1$ and $A_2$.

Significant Trait Associations with VCAKI Genotypes

Two alleles, A and C, are involved in genotypes which show association with traits [Breeding Value Total Number Born (BVTNB), Breeding Value Litter Weight (BVLWT), Average Number Born (AVNB), Average Number Weaned (AVNW), Average Weaning Weight (AVWW) and Weaning Weight Per Pig (WW/PIG)] in PIC line 19. Two analyses were done; results are shown in Tables 2 and 3.

TABLE 2

The means and standard errors for each trait by each genotype.

| | TRAITS | | | | | |
|---|---|---|---|---|---|---|
| Genotype | BVTNB | BVLWT | AVNB | AVNW | AVWW | WW/PIG |
| CC (6[1]) | −0.08 ± 0.18[2] | 2.61 ± 1.73 | 9.92 ± 0.86 | 7.67 ± 0.60 | 98.33 ± 12.37 | 23.26 ± 1.47 |
| BC (57) | 0.08 ± 0.07 | 1.65 ± 0.52 | 10.02 ± 0.30 | 7.89 ± 0.23 | 101.02 ± 3.17 | 12.94 ± 0.29 |
| BB (115) | 0.05 ± 0.05 | 0.78 ± 0.35 | 9.47 ± 0.24 | 7.68 ± 0.13 | 94.66 ± 2.26 | 12.37 ± 0.22 |

TABLE 2-continued

The means and standard errors for each trait by each genotype.

| Genotype | BVTNB | BVLWT | AVNB | AVNW | AVWW | WW/PIG |
|---|---|---|---|---|---|---|
| AC (4) | 0.32 ± 0.13 | 0.59 ± 1.95 | 11.50 ± 2.1 | 8.83 ± 0.80 | 93.58 ± 16.60 | 10.79 ± 1.78 |
| AB (13) | 0.45 ± 0.18 | 0.90 ± 0.72 | 10.53 ± 0.50 | 7.80 ± 0.47 | 87.17 ± 9.82 | 11.19 ± 0.98 |

[1]The number of animals per genotype
[2]The standard error

TABLE 3

The means and standard errors of each trait by allele groups

| Genotype | BVTNB | BVLWT | AVNB | AVNW | AVWW | WW/PIG |
|---|---|---|---|---|---|---|
| A- (171) | 0.42 ± 0.152 | 0.83 ± 0.68 | 10.750.50 | 8.040.41 | 88.688.24 | 11.100.83 |
| — (178) | 0.060.04** | 1.120.28 | 9.660.18† | 7.74 ± 0.11 | 96.82 ± 1.83 | 12.50 ± 18† |
| BB (115) | 0.05 ± 0.05 | 0.78 ± 0.35 | 9.47 ± 0.24 | 7.68 ± 0.13 | 94.66 ± 2.26 | 12.37 ± 0.22 |
| B- (70) | 0.15 ± 0.07 | 1.51 ± 0.44 | 10.11 ± 0.26 | 7.870.21 | 98.453.18 | 12.610.30 |
| — (10) | 0.080.17 | 1.80 ± 1.27 | 10.55 ± 0.95 | 8.130.49 | 96.43 ± 9.40 | 11.61 ± 1.09 |
| CC (6) | −0.08 ± 0.18 | 2.61 ± 1.73 | 9.92 ± 0.86 | 7.67 ± 0.60 | 98.3312.37 | 12.151.47 |
| C- (61) | 0.090.07 | 1.580.50 | 10.120.31 | 7.950.26 | 100.53 ± 3.13 | 12.80 ± 0.42 |
| — (128) | 0.09 ± 0.05 | 0.79 ± 0.32 | 9.58 ± 0.22 | 7.69 ± 0.12 | 93.90 ± 2.25† | 12.25 ± 0.22 |

[1]The numbers of animals per genotype
[2]The standard error
**P < 0.01
†P < 0.1

In the first analysis, no significant associations were seen with any individual genotype group. This may be due to the low numbers of animals with specific genotypes such as A- and C-. This is a possible explanation because when groups of similar genotypes are combined (Table 3), we observe highly significant association (P<0.01) for AA versus the A-genotype animals for Breeding Value for Total Number Born (BVTNB) and association tending to significance (P<0.1) for Average Number Born (AVNB) and Pig Weaning Weight (WW/PIG). For BVTNB and AVNB, the A allele has a positive effect; for WW/PIG, the A allele has a negative effect. We also see association tending to significance for the CC versus C- versus—genotype for Average Weaning Weight of the litter (AVWW) and WW/PIG. In both traits the C-genotype is superior on these traits.

As such it has been demonstrated that there is significant genetic diversity of VCAM1 in the Line 19 population sampled, with three alleles and five genotypes identified. Two relatively rare alleles show some potentially interesting associations, with the A allele the most promising due to its rarity and stronger effect.

Materials and Methods for VCAM1 PCR test:

Primers:

forward primer 5'-TATCAGCCCTCCATAGTCACAT 3'
(SEQ ID NO:10)
reverse primer 5'-GAAATTGTTGTCCATGACCTTTAT 3'
(SEQ ID NO:11)

-continued

| PCR conditions: | |
|---|---|
| Cocktail Mix | 25 ul reaction |
| 10X PCR buffer | 2.5 ul |
| 25 mM MgCl1 | 1.5 ul |
| 1.25 mM dNTP's | 4 ul |
| 19 pmol/ul forward primer | 0.5 ul |
| 10 pmol/ul reverse primer | 0.5 ul |
| dd sterile H$_2$O | 11.75 ul |
| 5u/ul Taq Polymerase | 0.25 ul |

The above reagents should be mixed and added to each reaction tube. Add 4 ul of the 12.5 ng/ul genomic DNA next and then overlay with a drop of mineral oil.
Thermal Cycler Program:
1. 95° C. 4 min
2. 98° C. 1 min
3. 48° C. 1 min
4. 72° C. 1 min
5. 4 cycles to 2
6. 90° C. 1 min
7. 48° C. 1 min
8. 72° C. 1 min
9. 34 cycles to 6
10. 72° C. 5 min
11. 4° C. hold
12. end 5 ul of the PCR product plus 1.5 ul of 6× loading dye should be placed on a 2% agarose gel containing the ethidium bromide to check yield. Run at 120V for 45 min and visualize the amplified DNA on UV box. The full length of the PCR product is ~193 bp.

Gel Electrophoresies

Optimum amount of the PCR product (~5 ul, dependent on how good the DNA were amplified) plus 6× loading dye should be placed on 15% acrylamide/bis-acrylamide (37.5:1) gel.

| 15% Acrylamide gel Mix | 50 ml gel |
|---|---|
| 10% APS | 0.5 ml |
| 40% acryl/bis (37.5:1) | 19 ml |
| 5X TBE | 5 ml |
| dd sterile H₂O | 25.5 ml |

0.5×TBE should be used as running buffer. Run at 105V overnight (~17 hr, run the bromophenol blue dye to the bottom) at room temperature.

The A allele can be identified upon separation and identification of a fragment of approximately 193 bp by separation of undigested amplified products.

Identification of BB and CC genotype

BB and CC genotypes are not able to distinguish on the acrylamide gel. There are two ways to identify the BB and CC genotypes. The first one is a mixing experiment; mix equal amounts of the unknown BB/CC DNA with known AA or BB or CC DNA. Then run the last cycle (90° C. 1 minute, 48° C. 1 minute, 72° C. 6 minutes, 40° C. hold) of the VCAM PCR to denature the DNA and renatured to form heteroduplex AB, AC or BC. Then the unknown BB/CC could be identified. A second method is RFLP mapping. After sequencing the homologous AA, BB and CC genotypes, three different restriction enzyme maps were obtained, which were caused by several base pairs difference among these three genotypes (see sequence comparison in FIG. 2). Thus a second way to identify BB/CC is PCR-RFLP, TaqI digestion.

| Digestion Mix | 25 ml reaction |
|---|---|
| 20 u/ul TaqI | 0.5 ul |
| 10X buffer | 2.5 ul |
| DNA | x ul (~5 ul, dependent on how yield of the PCR amplification) |
| dd sterile H₂O | 22-x ul |

Incubate the samples at 65° C. overnight

The digest product plus 5 ul 6× loading dye should be loaded on 2% agarose gel containing ethidium bromide. Run 120V for 1 hour. The TaqI RFLP is to generate 82 bp, 114 bp fragments in C allele and remaining 193 bp uncut in B allele (C allele has 3 additional base pairs).

EXAMPLE 2 (VCAM)

DNA Sequencing of VCAM1 Alleles

Two primers flanking the 193 bp VCAM1 PCR fragment were designed. The primer sequences were:

```
forward primer:  5'-TTGAATGCAGTGAACTCTTG 3' (SEQ ID NO:12)
reverse primer:  5'-AGTCAACCCAGTTCTTTCTT 3' (SEQ ID NO:13)
```

The genomic DNA of known AA, BB and CC animals were PCR amplified and sequenced using the above two primers.

The reagent mix of PCR reaction and the PCR program are similar to the previous reaction; only need to change the two primers to this new pair and change the annealing temperature of the program to 50 C:

Thermal Cycler Program to Amplify for Sequencing PCR Products 1. 95° C. 4 min
2. 94° C. 1 min
3. 50° C. 1 min
4. 72° C. 1 min
5. 4 cycles to 2
6. 90° C. 1 min
7. 50° C. 1 min
8. 72° C. 1 min
9. 34 cycles to 6
10. 72° C. 5 min
11. 4° C. hold
12. end The results are shown in FIG. 3.

EXAMPLE 3 (VCAM)

VCAM1 was genotyped according to the PCR test disclosed herein. The results are shown in Table 4.

TABLE 4

| | Genotype Frequencies | | | | |
|---|---|---|---|---|---|
| Breed | AA | AC | BC | BB | CC |
| Duroc n = 17 | 0.00 | 0.00 | 0.59 | 0.35 | 0.06 |
| Landrace n = 10 | 0.00 | 0.10 | 0.10 | 0.40 | 0.00 |
| Large White n = 12 | 0.00 | 0.00 | 0.00 | 1.00 | 0.00 |
| Meishan n = 12 | 1.00 | 0.00 | 0.00 | 0.00 | 0.00 |
| Wild Boar n = 2 | 0.00 | 0.00 | 0.50 | 0.50 | 0.00 |

VCAM1 was first genotyped in the top 20 and bottom 20 individuals for two traits, AV NB and AV WW in L19 individuals. The results are depicted in Table 5.

TABLE 5

| | Allele Frequencies | | | |
|---|---|---|---|---|
| | AV NB n = 20/20 | | AV WW n = 20/20 | |
| Allele | High | Low | High | Low |
| A | 0.075 | 0.05 | 0 | 0.125 |
| B | 0.75 | 0.675 | 0.875 | 0.700 |
| C | 0.175 | 0.275 | 0.125 | 0.175 |

For the high AV NB group there was a higher frequency of the A and B alleles compared to the low AV NB group. For the high AV WW group there was a higher frequency of the B allele than that in the low AV WW. A preliminary analysis of genotype effects were estimated by simple averaging of the individual animal values among all 78 animals so far typed for AV NB. The AC animals (n=4) were 11.50÷2.1, AB animals (n=6) were 11.28÷0.55, BB animals (n=40) were 9.10÷0.64, BC animals (n=26) were 9.65÷0.63, and CC animals (n=2) were 11.75÷0.25. Ignoring the CC animals, those involving the A alleles were best.

Yet another analysis was performed for VCAM1 effects for the first parity in L94 animals. In L94, 24 sister groups were tested (89 animals), and 18 litter groups were informative (sisters with different VCAM1 genotypes were found in 18 litters). Mean differences between the six genotypes were not significant for total number born or number born alive though females with the three genotypes involving the A allele again had the largest litter size.

EXAMPLE 4 (RBP4)

Linkage Mapping of the Retinol-Binding Protein 4 (RPB4) Gene to Porcine Chromosome 14

Map positions: Loci order of a portion of the distal end of Chromosome (Chr) 14: -ACTN2-1.7-ACTA1-2.7-PLAU-0-SW210-8.2-S0169-9.9-S0072-11.1-S0007-7.3-RBP4-16.2-S0116-20.0-Sw761-36.1-S0015.

Method of mapping: Six three-generation PiGMaP families of Meishan x Large White and European Wild Boar x Large White pigs. Archibald, A. et al., 1995. Mamm. Genome 6:157–175.

Molecular reagents: The porcine RBP4 gene probe was obtained by RT-PCR amplification of a 311-bp fragment from day 12 porcine blastocysts with primers designed based on pig cDNA sequences. The 5' primer (5'-TTCCGAGTCAAAGAGAACTTCG-3') (SEQ ID NO: 14) represents nucleotides 79–100, and the 3' primer (5'-TCATAGTCCGTGTCGATGATCC-3') (SEQ ID NO: 15) represents nucleotides 368–389. Trout, W., et al. 1991, Mol. Endocrinol. 5:1533–1540. Amplified product was purified and radiolabeled with $^{32}$P by random priming.

Allele detections: A SacI polymorphism was detected in pig genomic DNA by hybridization of Southern blots with the labelled 311 bp pig RBP4 fragment at a final wash stringency of 0.7×SSC and 0.2% SDS at 65° C. Autosomal Mendelian inheritance was observed in two polymorphic fragments detected at 12.1 kb and 7.8 kb. Sixty-two unrelated pigs from eight breeds were genotyped for RBP4. Frequencies of the 12.1-kb fragment were 0.55 in Landrace (n=10), 0.75 in Duroc (n=10), 1.0 in Yorkshire (n=5), 0.50 in Chester White (n=4), 0.59 in Large White (n=11), 1.0 in Hampshire (n=5), 0.80 in Meishan (n=15), and 1.0 in Wild Boar (n=2).

Previously identified homologs: Human RBP4 maps of 10q23–24 Rocchi, M., et al. 1989, Somat. Cell Mol. Genet. 15:185–190, and mouse Rbp-4 is localized to the distal end of Chr 19 Chainani, M., et al., 1991, Genomics 9:376–379.

Discussion: Retinol-binding protein is a major secretory product of the pig conceptus prior to implantation. Increased production of RBP4 during the rapid morphological developmental period of pig blastocyst elongation, which is a critical period for embryonic survival, suggests that RBP4 may be an interesting candidate gene for investigation of QTL for reproduction in pigs.

Linkage analysis was performed with the CRIMAP version 2.4 software package. The two-point linkage analysis produced significant lod scores (>3.0) of RBP4 with loci S0007, S0116, and SW210 on porcine Chr 14 (Table 6). The order of the loci on our map is in agreement with the new loci arrangement of the PiGMaP map of Chr 14 according to Kapke and associates, (Kapke, P., et al., 1995, Anim. Genet., in press) with the exception of the rearrangement of loci S0007 and S0072. The addition of RBP4 to the revised PiGMaP map further increases the sex-averaged map length from 193 cM to 202 cM. Placement of RBP4 on Chr 14 strengthens the homology between porcine Chr 14 and human Chr 10. Johansson, M., et al., 1995, Genomics, 25:682–690.

TABLE 6

Results of the two-point linkage analysis for RBP4

| Marker 1 | Marker 2 | Recombination fraction | Lod score |
|---|---|---|---|
| RBP4 | S0007 | 0.07 | 17.02 |
| RBP4 | S0116 | 0.21 | 4.63 |
| RBP4 | SW210 | 0.27 | 3.50 |

EXAMPLE 5 (RARG)

Linkage Mapping of the Retinoic Acid Recptor-γ Gene to Porcine Chromosome 5

The porcine retinoic acid receptor-γ gene (RARG) has been mapped by restriction fragment length polymorphism analysis to porcine chromosome 5. The placement of RARG distal to the diacylglycerol kinase gene increases the length of the existing map (PiGMaP) and adds a fifth type-I marker to this sparsely mapped chromosome. This augments the homology of pig chromosome 5 and human chromosome 12 established by previous comparative mapping.

Recent preliminary expression studies of porcine RAR mRNA in elongating porcine blastocysts (day 10–12 of pregnancy) show that mRARG is expressed in all stages of blastocyst elongation, with the highest level of expression during ≧8 mm to early tubular stage (Yelich et al. 1995). Mouse RAR-γ is also strongly expressed in mouse derived embryo-carcinoma cells (Zelent et al. 1989). RAR-γ displays high levels of sequence conservation across species. The RAR-γ gene has been mapped to chromosome 12q13 in human, chromosome 15 band F in the mouse and chromosome 7 in the rat (Mattei et al. 1991). Based on the location of human and mouse RARG, it was postulated that RARG would map to porcine chromosome 5.

The investigation of RARG was initiated by designing primers for reverse transcriptase polymerase chain reaction (RT-PCR) analysis of RARG gene expression in early pig embryos (Yelich et al. 1995). Primers were designed based on cDNA sequence homology between mouse and human. The 5'-primer (5'GGCATGTCCAAGGAAGCTGT3') (SEQ ID NO: 16) represents human nucleotides 874–893 (Krust et al. 1989) and murine nucleotides 775–794 (Zelent et al. 1989). The 3'-primer (5'GTTCTCCAGCATCTCTCGGAT3') (SEQ ID NO: 17) represents human nucleotides 1648–1668 and murine nucleotides 1549–1569. Total mRNA (o.5 μg) from day 12 porcine blastocysts was converted to cDNA (20 μl final volume) with oligo dT primer and M-MLV reverse transcriptase. PCR conditions (25 μL final volume) were 0.75 mM MgC12, 100 μM each dNTP, 0.3 μM each primer, 1 μl of cDNA and 0.625 U Taq DNA polymerase. The first PCR cycle was 2 minutes at 95° C., 1 minute at 60° C., 2 minutes at 72° C.; 34 cycles of 1 minute at each temperature of 94° C., 60° C., and 72° C. followed, ending with a 9 minute extension phase at 72° C. The PCR product (795 bp) was purified and radiolabeled with $^{32}$P by random priming. Membranes of digested genomic DNA of American and Chinese breeds and PiGMaP family DNA (Chinese, European and Wild Boar) (Archibald et al. 1995), prepared by standard protocol, were hybridized overnight at 65° C. by standard methods and washed at a final stringency of 0.5× SSC at 65° C.

Figure 4A:
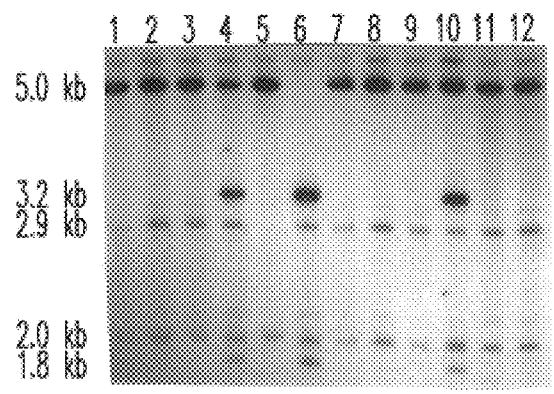
FIGS. 4A and 4B are RFLP analyses showing the Mendelian segregation of the pig RARG fragments in a three generation PiGMaP family. (4A) Stu I digest Lanes 1–2, 3–4, and 5–6 represent three $F_0$ matings of Large White sires to Meishan dams, which produced $F_1$ in lanes 7,8–9, and 10 respectively. The cross of $F_1$ in lanes 7 and 8 produced the $F_2$ shown in lanes 11 and 12. (4B) SAC I digest. Lanes 1–2 and 3–4 represent $F_0$ matings of Meishan sires to Large White dams which produced $F_1$ in lanes 5 and 6–7, respectively. The cross of $F_1$ in lanes 5 and 6 produced the $F_2$ in lanes 8–10.

A polymorphism was detected with membranes containing DNA of StuI and SacI digestions. The hybridization of StuI digests with the pig cDNA RARG probe revealed six fragments (FIG. 4a). The 6.0, 2.9 and 2.0 kb fragments were monomorphic. The 5.0, 3.2 and 1.8 kb fragments were polymorphic. Autosomal Mendelian segregation of the 5.0 and 3.2+1.8 kb fragments was observed in ten, three-generation families of Meishan X Large White, European Wild Boar X Large White, and Chinese X American breed crosses. Fifty-five unrelated pigs from nine breeds were also genotyped for RARG. Frequencies of the 5.0 kb fragment were 0.56 in Chinese (n=15), 0.47 in Large White (n=15), 0.08 in Duroc (n=6), 0.13in Landrace (n=4), and 0.13 in Hampshire (n=9). Two Wild Board and four Stress-line pigs were homozygous for the 3.2+1.8 kb fragments.

Figure 4B:
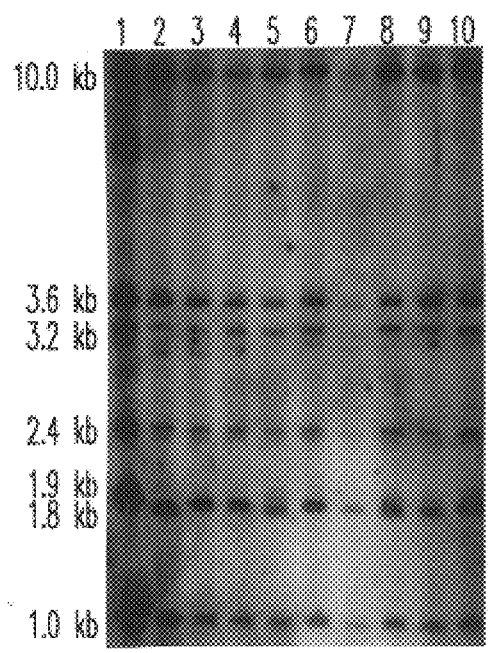

The hybridization of the SacI digests produced eight fragments (FIG. 4b). The 10, 3.6, 3.2, 2.4 and 1.0 kb fragments were monomorphic, while the 1.9 and 1.8 kb fragments were polymorphic and allelic. Thirty-nine unrelated pigs from six breeds were genotyped for RARG. Frequencies of the 1.9 kb fragment were 0.50 in Meishan (n=6), 0.10 in Yorkshire (n=5), 1.0 in Duroc (n=7), 0.64 in Landrace (n–11), 0.20 in Hampshire (n=5), and 0.50 in Chester White (n=5). An additional, non-allelic 7.1 kb fragment was only observed in one Chester White and three Meishan animals.

The linkage analysis was performed using the software package CRIMAP version 2.4 (Green et al. 1990) with data from PiGMaP ResPig Database (Archibald et al. 1995). Pairwise linkage analysis was performed with the TWOPOINT option of CRIMAP for all loci under the assumption of equal recombination rates in the two sexes. A LOD score of 3.0 was considered the significance threshold for all pairwise analyses. An initial ordered framework of loci was used and the new locus, RARG, was inserted into the possible positions based on the linkage results of the pairwise analysis. The best position for RARG was determined with large log 10 likelihoods. A multipoint map was built with BUILD, FLIPS and FIXED options of CRIMAP.

Figure 5:
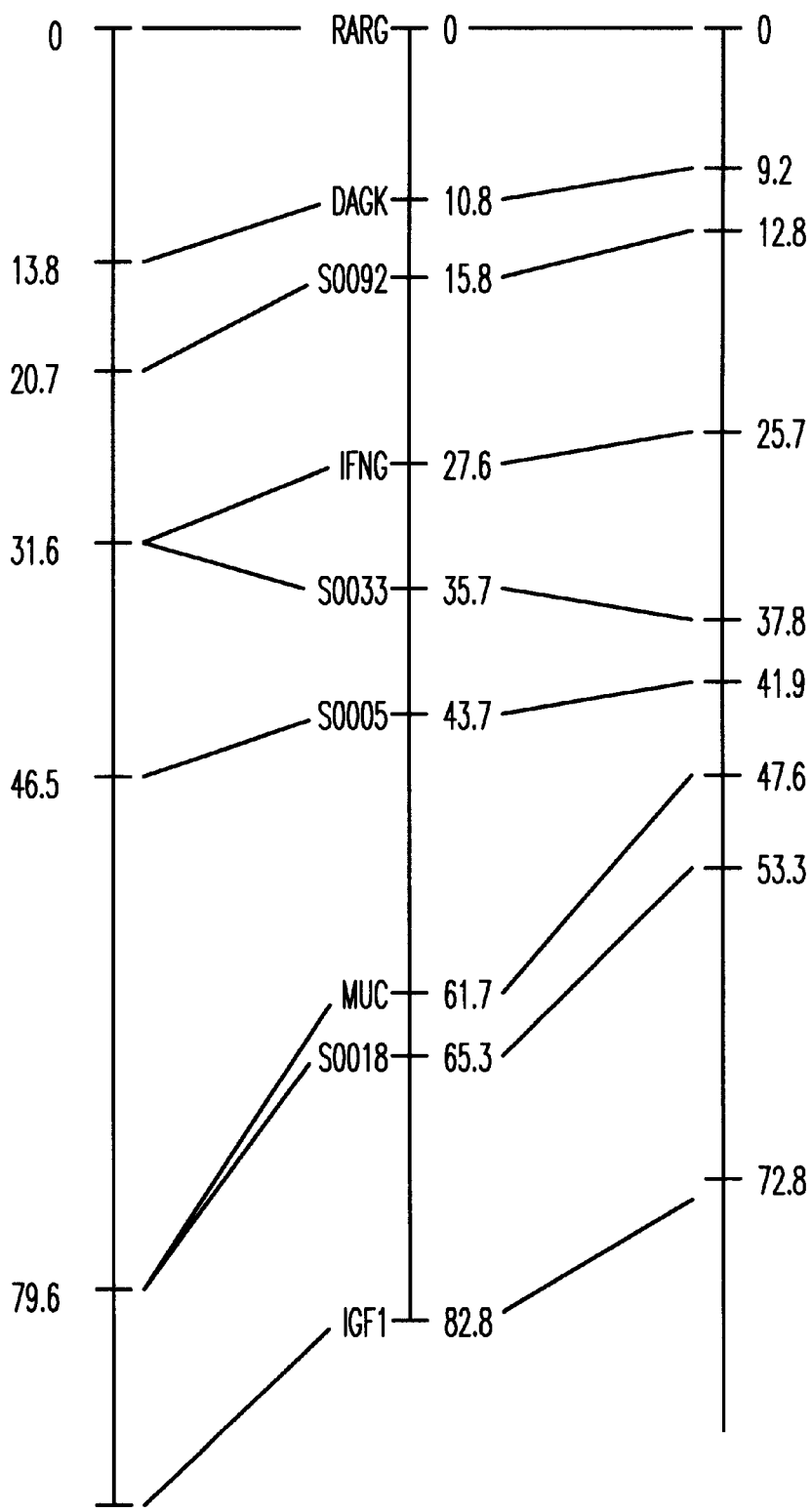
FIG. 5 depicts a multipoint linkage map of pig chromosome 5. The female map is on the left, the sex-averaged map in the middle, and male map on the right. (Distances in Kosambi cM) are given on the left and right sides of the maps.

The two-point linkage analysis with 101 informative meioses (for the Sacd polymorphism) produced significant LOD scores (>3.0) and recombination fraction values (respectively, in parentheses) between RARG and the following loci: diacylglycerol kinase gene (DAGK) (10.0, 0.07), S0092 (12.29, 0.09), interferon gamma (1FNG) (5.80, 0.19), and S0033 (4.02, 0.05). The best multipoint map (log likelihood =–157.0) places RARG distal to DAGK by 10.8 cM (FIG. 5). Two other maps place RARG between S0092 and IFNG (log likelihood=–159.7) and between DAGK and S0092 (log likelihood=–160.4). Three multipoint maps with nearly equal log likelihood values were built using 33 informative meioses from the StuI polymorphism. The order of these three maps is in agreement with the results from the SacI analysis. The SacI-based map was chosen since it was built from the largest number of informative meioses and it had the largest log likelihood value (FIG. 5).

The placement of RARG on pig chromosome 5 augments the reported homology between pig chromosome 5 and human chromosome 12 (Johansson et al. 1995). The PiGMaP map (Archibald et al. 1995) and the USDA map (Rohrer et al. 1994) show chromosome 5 to have only four type-I markers, including DAGK, 1FNG, and insulin-like growth factor 1 (IGF1). Mapping RARG distal to DAGK increases the chromosome length of the existing PiGMaP map. On the USDA map, RARG would probably map between the existing marker Swr453 at 0 cM and DAGK at 21 cM (Rohrer et al. 1994). The arrangement of the DAGK, 1FNG, and RARG loci is in agreement with the comparative map of human chromosome 12, where the loci order is RARG (12q13), DAGK (12q13.3) and IFNG (12q24.1) (Mattei et al. 1991; Hart et al. 1994; Trent et al. 1982).

EXAMPLE 6 (RARG and RBP4)
Association of Polymorphisms with Litter Size

Partial CDNA fragments of these genes were used for RFLP detection on Southern membranes containing digested reference family DNA. The RARG analysis produced three fragments (two alleles) on StuI membranes at 5.0 kb, 3.2 kb and 1.8 kb. SacI membranes probed with RBP4 showed two allelic fragments at 12.1 kb and 7.8 kb. RARG and RBP4 were mapped by linkage analysis to chromosomes 5 and 14, respectively. To illustrate effects of these genes, two French Large White lines were genotyped at these loci. The first line consisted of French hyperprolific (LWH) pigs (32 sows with 216 litter records). The second line consisted of French control (LW) pigs (27 sows with 242 litter records). The average additive effect of the gene, estimated as the linear regression of litter size on genotype, was $0.21\pm0.30$ pigs per litter increase in LWH and $0.14\pm0.38$ pigs per litter for the RARG 5.0 kb allele. RBP4 had an additive gene effect of $0.52\pm0.30$ in LWH and $0.45\pm0.43$ in LW for the 7.8 kb allele. The allelic substitutive effect for litter size ranged from 5 to 17% of the phenotypic STD. These initial data demonstrate that alleles of RARG and RBP4 may account for increased litter size in the pig.

EXAMPLE 7 (RBP4)
PCR-RFLP Test for MspI polymorphism

Based on the identification of polymorphism in the RBP4 gene a PCR test was developed.

| Primers | |
| --- | --- |
| LM2419 5'-GAGCAAGATGGAATGGGTT-3' (SEQ ID NO: 18) | |
| LM2420 5'-CTCGGTGTCTGTAAAGGTG-3' (SEQ ID NO: 19) | |
| PCR conditions: | 25 µL reaction |
| Mix 1: | |
| 10X Promega Buffer | 2.5 µL |
| 25 mM MgCl$_2$ | 1.5 µL |
| 10 mM dNTP's (Boehringer Mannheim) | 0.5 µL |
| 16 pMol LM2419 (100 ng/µL) | 0.5 µL |
| 16 pMol LM2420 (100 ng/µL) | 0.5 µL |
| dd sterile H$_2$O | 12.5 µL |
| 25 ng genomic DNA (12.5 ng/µL) | 2.0 µL |
| Taq Mix: | |
| dd sterile H$_2$O | 4.9 µL |
| 0.6 U Taq Polymerase (Promega) | 0.12 µL |

Combine 18 µL of Mix 1 and DNA in reaction tube. Overlay with Mineral Oil. Preheat on thermal cycler at 85° C. Add 5 ul of Taq Mix. Run the following PCR program:

| Step 1. | 93° C. 3 min |
| --- | --- |
| Step 2. | 93° C. 30 sec |
| Step 3. | 56° C. 45 sec |
| Step 4. | 72° C. 45 sec |
| Step 5. | Go to step 2 for 39 more cycles |
| Step 6. | 72° C. 5 min |
| Step 7. | 4° C. hold |

Check 5 µL of the PCR reaction on a standard 1% agarose gel to confirm amplification success and clean negative control. Product size is approximately 550 base pairs. Digestion can be performed directly in PCR tube.

| MspI Digestion Reaction | 30 µL reaction |
| --- | --- |
| Remaining PCR product | 20.0 µL |
| 10X NE Buffer 2 | 3.0 µL |
| 10U Msp I enzyme (20 U/µL) | 0.1 µL |
| dd sterile H$_2$O | 6.9 µL |

Make a cocktail of the buffer, enzyme and water. Add 10 µL to each reaction tube containing the DNA. Incubate at 37° C. overnight. Add loading dye directly to digestion reaction and load the total volume on a 3% NuSieve gel. The major bands for the AA genotype are 190 bp, 154 bp, and 136 bp; The BB genotype bands are 154 bp, 136 bp and 125 bp.

Analysis of the French lines showed that the new PCR test MspI ALLELE A=(old) SacI Allele 2.

Using the PCR-RFLP to genotype University of Nebraska high ovulating and control lines, the results by line show:

|  | A | B |
|---|---|---|
| Index | .50 | .50 |
| Control | .47 | .53 |

PIC Line 19 Animals (with appropriate records) analyzed with the Msp I test are shown in Tables 7 and 8 below.

TABLE 7

| AVE NB | Genotype N | Mean | Std Err |
|---|---|---|---|
| AA | 93 | 10.178 | 0.237 |
| AB | 98 | 9.292 | 0.275 |
| BB | 18 | 9.722 | 0.511 |

TABLE 8

| EBV TNB | Genotype N | Mean | Std Err |
|---|---|---|---|
| AA | 93 | 0.160 | 0.062 |
| AB | 98 | 0.034 | 0.049 |
| BB | 18 | 0.108 | 0.112 |

The data grouped for litter size is shown below.

|  | AA | AB | BB | A | B |
|---|---|---|---|---|---|
| Large Litter | .62 | .36 | .04 | .78 | .22 |
| Small Litter | .24 | .64 | .12 | .56 | .44 |

EXAMPLE 8 (RBP4 and RARG)

Gene frequency and allelic effects in specialized populations of hyperprolific and "control" sows were conducted according to the methods disclosed herein. The populations consist of about 30 sows with 7–9 parities each. Initial analyses were completed on the average litter size over the first four parities. The RARG allele 1, a Southern membrane RFLP from hybridization of pig RARG CDNA probe produced by RT-PCR with primers 5'GGCATGTCCAAGGAAGCTGT-3' (SEQ ID NO: 16) and 5'GTTCTCCAGCATCTCTCGGAT-3' (SEQ ID NO: 17) to membranes containing Stu I digested genomic DNA. A 5.0 kb fragment with Stu I digestion and primers, as disclosed on page 31, had an additive effect of 0.2 pigs more born and the RBP4 allele A a 190 bp, 154 and 136 bp fragment with MSP I digestion and primers LM2419 and LM2420 had an average additive effect of 0.5 more pigs born.

EXAMPLE 9 (HTMR1A)

Mapping and Polymorphish Identification

Recent work on HSA4 has included the mapping of MTNR1A to 4q35.1. The mouse homologue maps to the proximal portion of chromosome 8 (Slaugenhaupt et al. 1995). No genes have been mapped in the pig which correspond to the distal portion of HAS4q, so mapping of MTNR1A was sought to extend the defined boundary of the chromosomal rearrangement of SSC8 (Ellegren et al. 1993). The gene was also mapped in sheep and cattle to further define previously established synteny in these species. The information of the intron-exon boundary in MTNR1A was used to develop a polymerase chain reaction (PCR) primer strategy to design degenerate and specific primers for the amplification of partial coding sequence fragments of this gene from genomic pig, sheep and cattle DNA.

Materials and methods

PCR and RFLP in pig. Degenerate primers for PCR were designed from regions of high amino acid conservation in Exon II of the human and sheep sequence. The forward primer was 5' ATI ACI GGI ATI GCI ATA/T/C AAT/C C/AGI/C TA 3' (SEQ ID NO: 20) and the reverse was 5' TTI AA/GA/G CAI C/GA/TA/G TTA/G TAI GCC AT 3' (SEQ ID NO: 21). These were used with 50 ng of pig genomic DNA in a 50 µL PCR reaction of (50 mM KCl, 10 mM tris-HCl, 0.1% Trition X-100) 200 µM each dNTP, 2.5 mM $MgCl_2$, 0.2 µM each primer and 0.6 U Taq polymerase (Promega, Madison, Wis., USA). Conditions were 93° C., 3 min, followed by 5 cycles of: 93° C., 30 s; 47° C., 2 min; 72° C., 3 min, then 10 cycles of: 93° C., 30 s; 59° C., 2 min; 72° C., 3 min, and then 24 cycles of: 93° C., 30 s; 63° C., 2 min; 72° C., 3 min. The program ended with a 5 minute extension at 72° C. Products were separated on a 2% agarose gel, and a major band was observed at approximately 520 bp. This product was gel-purified and cloned with the pT7 Blue T-Vector Kit (Novagen, Inc., Madison, Wis., USA). Direct colony PCR confirmed positive clones, and duplicates of two animals were sequenced with kit primers by automated dideoxy terminator cycle sequencing at the Iowa State University DNA Sequencing and Synthesis Facility. The 520 bp insert was excised from the plasmid using the restriction enzymes SpeI and SacI, gel-purified and radiolabeled with $^{32}P$ by random priming. Membranes containing DNA of American and Chinese breeds and PiGMaP DNA (Archibald et al. 1995), prepared by standard protocol, were hybridized with the MTNR1A probe overnight at 65° C. by standard methods and washed at a final stringency of 0.7×SSC at 65° C. Additionally, pig specific primers were designed from the sequence information generated. These primers were 5' TAT TGC TAC ATC TGA CAC AGT C 3' (SEQ ID NO: 22) which corresponds to amino acid residues 142–148 (YCCICHS) in the sheep melatonin receptor sequence (Reppert et al. 1994), and 5' GCC ACA AAC AGC CAC TCT GGG A 3' (SEQ ID NO: 23) which corresponds to residues 288–294 (IPEWLFV). The PCR conditions were changed by a reduction of $MgCM_2$ concentration to 1.5 mM and the cycling conditions were 93° C., 3 min, followed by 35 cycles of: 94° C., 30 s; 64° C., 1 min; 72° C., 45 s, plus a 5 minute extension at 72° C. A 461 bp fragment was produced. These pig specific primers were used in PCR experiments on the porcine somatic cell hybrid DNAs. This somatic cell hybrid panel is composed of 27 independent clones that have been characterized at the cytogenetic and molecular levels (Robic et al. 1996; Yerle et al. 1996). 50 ng of porcine genomic, rodent genomic and hybrid DNAs were used as template and amplified in 25 µl reactions under the same conditions used to produce the 461 bp product. The pig primers were also used on a pig YAC library containing approximately 33,000 clones averaging 280 kb in size, corresponding to a three-fold coverage of the pig haploid genome (Rogel-Gaillard et al. 1996). For the melatonin primer set, PCR conditions were an initial denaturation step at 93° C. for 3 min, then 35 cycles of 93° C., 30 s; 64° C. 1 min: 72° C. 45 s. Taq I polymerase was from Eurogentec. For positive clone size determination, a 3 day culture of the YAC was embedded in 100 µl of 0.5% low melting gel agarose and the plug was processed as described (Albertsen et al. 1989) using 3 units per ml zymolyase 20-T and 0.5 mg/ml proteinase K. The plug was submitted to PFGE in 1% agarose gel 0.5×TBE buffer for 20 h at 80° C. using a 70 second switch time using a LKB Pharmacia apparatus. The DNA fragments were transferred onto nylon membrane (Nytran, Schleicher and Schuell) and hybridized with 32P total swine genomic DNA as a probe. The DNA labeling, hybridization and washings were performed as described (Nunes et al. 1994). Native AB1380 yeast chromosomes and lambda phage DNA were run as controls for sizing. For the fluorescent in situ hybridization (FISH) experiment, the YAC DNA was prepared by proteinase K digestion followed by 2 phenol and 3 chloroform extractions and ethanol precipitation. FISH of the YAC clone to porcine metaphases was performed mainly according to the procedure described previously for the localization of cosmids (Yerle et al. 1994). Briefly, 200 ng of total yeast DNA were labeled by incorporation of biotinylated 16-dUTP (Boerhinger) in a random priming experiment. For suppression of background caused by repetitive sequences, the biotinylated YAC probe, sonicated pig genomic competitor DNA (50-fold excess) and salmon sperm DNA (75-fold excess) were prehybridized 3 hours at 37° C. Hybridization was detected using avidin conjugated to fluorescein (FITC). The signals were amplified once by incubation of the slides with biotinylated goat anti-avidin, followed by a final incubation with avidin-FITC.

PCR and RYLP in sheep

A portion of sheep MTNR1A was amplified from genomic DNA using primers designed from existing sheep sequence (Reppert et al. 1995). The primers were 5' TGT-GTTTGTGGTGAGCCTGG 3' (SEQ ID NO: 24) corresponding to amino acids residues 80–85 and 5' ATG-GAGAGGGTTTGCGTTTA 3' (SEQ ID NO: 25) at residues 348–353 (FIG. 9). PCR conditions were the same as with the pig-specific primers, with the exception of 1.5 mM $MgCl_2$ and a 60° annealing temperature. A 824 bp product was amplified and purified for sequencing. Several restriction enzymes were tested to identify an RFLP in this product, and the sheep AgResearch International Mapping Flock (IMF) and other breeds were genotyped.

PCE and RFLP in cattle

The sheep primers were used with cattle genomic DNA under the same PCR conditions. A major product of 824 bp was produced, gel-purified and sequenced. The PCR product was digested with several restriction enzymes to test for polymorphisms in the product, and a cattle reference family and several breeds of cattle were genotyped. The sheep primers were also used under the same PCR conditions with a panel of 20 bovine x rodent somatic cell hybrids representing the 31 domestic cattle syntenic groups (Womack and Moll 1986; Womack et al. 1993).

Linkage analysis

All linkage analyses were performed using the software package CRIMAP version 2.4 (Green et al. 1990) with data from PiGMaP ResPig Database (Archibald et al. 1995). Pairwise linkage analysis was performed with the TWOPOINT option of CRIMAP for all loci under the assumption of equal recombination rates in the two sexes. A LOD score of 3.0 was considered the significance threshold for all pairwise analyses.

Sequencing

The sequencing of the pig PCR product confirmed a 153 amino acid MNTR1A product which had 83% amino acid identity to sheep MTNR1A, 84% identity to human MTNR1A, and only 63% identity to human MTNR1B sequence (Reppert et al. 1995). Identity computations were performed at the NCBI using the BLAST network service. In the sheep, the sequence matched published sheep sequence. Sequencing of the cattle product confirmed a MTNR1A product which had 97% amino acid identity to sheep MTNR1A, 84% identity to our pig sequence, 84% identity to human MTNR1A, and only 60% identity to human MTNR1B sequence. A comparison of the percent amino acid identity across species is shown in FIG. 9.

Polymorphisms and mapping

Figure 10A:
FIG. 10, Panels A–C depict the MTNR1A polymorphisms in pig, sheep and cattle. A) The segregation of the 4.3 kb and 3.9 kb TaqI alleles in a porcine reference family. The sire in lane 1 and dam in lane 2 produced the offspring in lanes 3–10. B) The genotypes of the sheep RsaI polymorphism. Only the 503 bp, 295 bp, and 290 bp fragments are shown. C) The bovine DrdI polymorphism. Lane 1 is uncut PCR product, and lanes 2–4 represent the three genotypes.
Figure 10B:
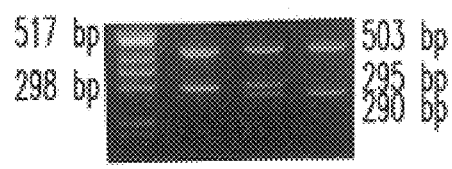
Figure 10C:
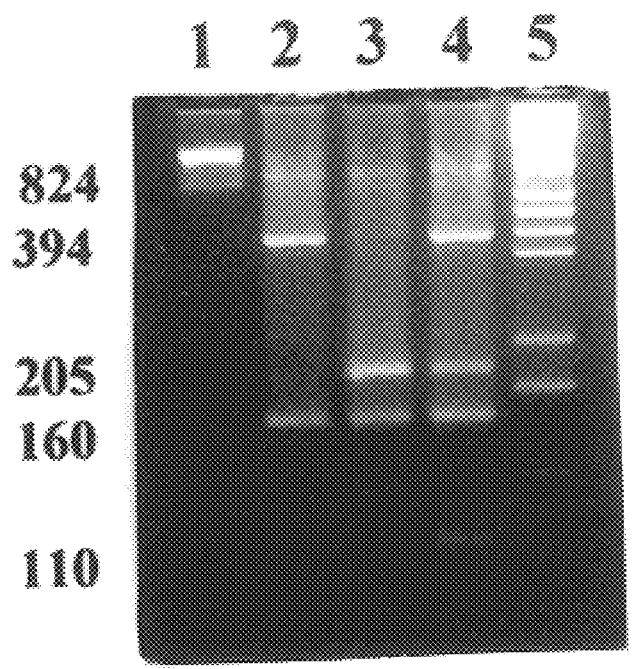

The hybridization of Taq I membranes with the pig MTNR1A probe revealed three fragments at approximately 4.3, 4.2, and 3.9 kb which segregated with a pattern consistent with Mendelian inheritance through three PiGMaP three-generation families (Archibald et al. 1995) (FIG. 10). Additional alleles at 3.8 and 2.9 kb were observed on membranes containing DNA from several individuals from nine breeds of pig. Allele frequencies were calculated for these breeds and are shown in Table 9.

TABLE 9

Allele frequenices of the Taq I RFLP in several breeds of pigs.

| | | Frequency of each allele | | | | |
|---|---|---|---|---|---|---|
| Breed | Number | 4.3 kb | 4.2 kb | 3.9 kb | 3.8 kb | 2.9 kb |
| Meishan | 14 | 0.04 | 0.04 | 0.93 | 0.00 | 0.00 |
| Minzhu | 3 | 0.00 | 0.00 | 0.67 | 0.00 | 0.33 |
| Wild Boar | 2 | 0.00 | 0.00 | 1.00 | 0.00 | 0.00 |
| Large White | 11 | 0.23 | 0.00 | 0.77 | 0.00 | 0.00 |
| Yorkshire | 8 | 0.19 | 0.00 | 0.81 | 0.00 | 0.00 |
| Chester White | 8 | 0.38 | 0.00 | 0.38 | 0.25 | 0.00 |
| Hampshire | 11 | 0.00 | 0.23 | 0.73 | 0.04 | 0.00 |
| Landrace | 11 | 0.00 | 0.00 | 0.86 | 0.00 | 0.14 |
| Duroc | 10 | 0.00 | 0.00 | 0.65 | 0.35 | 0.00 |

Results of the two-point linkage analysis of the porcine Taq I RFLP showed significant LOD scores with microsatellite S0296 previously mapped on the PiGMaP chromosome 17 map (Archibald et al. 1995) and with several microsatellites from the USDA chromosome 17 map (Rohrer et al. 1994) (Table 10).

TABLE 10

Two-point linkage analysis results for the pig, sheep, and cattle MTNR1A loci.

| | Recombination fractions | | | | | | | | |
|---|---|---|---|---|---|---|---|---|---|
| Marker | .001 | .01 | .05 | .10 | .15 | .20 | .25 | .30 | .35 |
| Pig | | | | | | | | | |
| SWR1004 | 17.44 | 18.13 | 17.42 | 15.92 | 14.23 | 10.55 | 8.59 | 6.56 | 4.46 |
| SW24 | 8.43 | 10.25 | 10.82 | 10.34 | 9.55 | 8.59 | 7.5 | 6.28 | 4.93 |
| S0296 | 0.03 | 3.88 | 6.04 | 6.39 | 6.20 | 5.76 | 5.14 | 4.37 | 3.48 |
| SW1031 | −32.05 | −14.28 | −2.73 | 1.34 | 3.09 | 3.85 | 4.03 | 3.80 | 3.25 |
| SW840 | −23.36 | −9.58 | −0.77 | 2.18 | 3.34 | 3.73 | 3.68 | 3.34 | 2.77 |
| Swr1120 | −3.28 | 0.62 | 2.97 | 3.59 | 3.67 | 3.51 | 3.20 | 2.77 | 2.23 |

TABLE 10-continued

Two-point linkage analysis results for the pig, sheep, and cattle MTNR1A loci.

| Marker | Recombination fractions | | | | | | | | |
|---|---|---|---|---|---|---|---|---|---|
| | .001 | .01 | .05 | .10 | .15 | .20 | .25 | .30 | .35 |
| Sheep | | | | | | | | | |
| OarCP93 | | | | | | | | | |
| Cattle | | | | | | | | | |
| In16 | 20.44 | 22.00 | 21.41 | 19.46 | 17.16 | 14.69 | 12.08 | 9.37 | 6.62 |
| INBEL191 | 19.84 | 21.40 | 20.79 | 18.83 | 16.54 | 14.09 | 11.53 | 8.89 | 6.22 |
| R209 | 13.24 | 16.80 | 17.62 | 16.28 | 14.39 | 12.24 | 9.94 | 7.54 | 5.11 |
| BM3507 | −17.64 | −1.12 | 8.60 | 10.93 | 11.05 | 10.21 | 8.83 | 7.09 | 5.10 |
| 1179 | −10.66 | 0.98 | 7.74 | 9.25 | 9.18 | 8.43 | 7.28 | 5.87 | 4.29 |
| CS36 | −24.26 | −9.54 | −0.31 | 2.58 | 3.54 | 3.69 | 3.38 | 2.77 | 1.97 |
| CS43 | −26.96 | −11.25 | −1.38 | 1.76 | 2.85 | 3.10 | 2.89 | 2.40 | 1.71 |

Figure 11A:
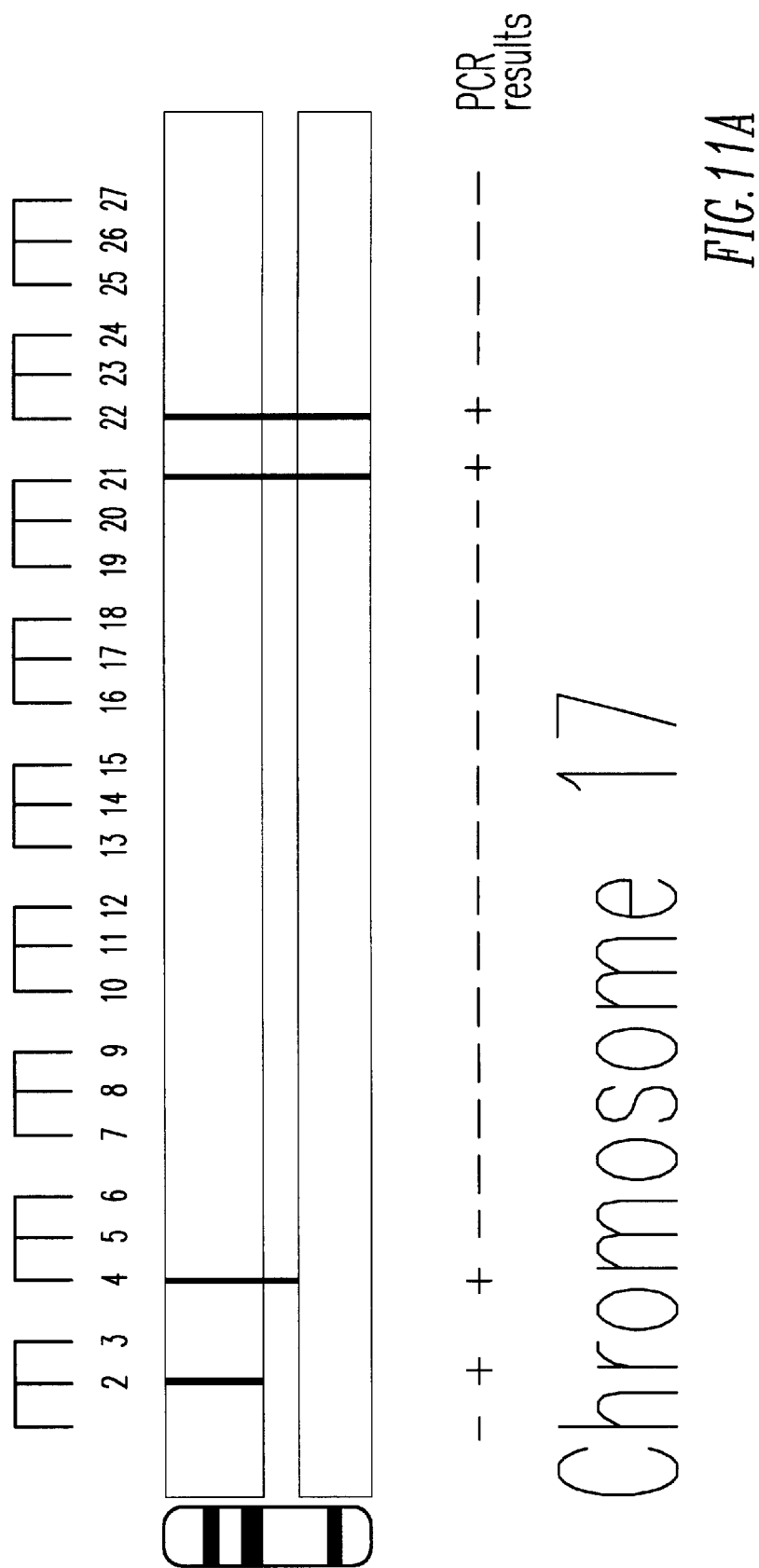
FIGS. 11A and 11B depict physical mapping results in the pig. (11A) Results of PCR experiments with the porcine somatic cell hybrid panel localized MTNR1A to chromosome 17q1.1–q1.4 region. (11B) Results of the YAC FISH experiment showed a strong fluorescent double spot was detected on pig chromosome 17 in the q1.2 region in more than 90% of the metaphases analyzed.
Figure 11B:
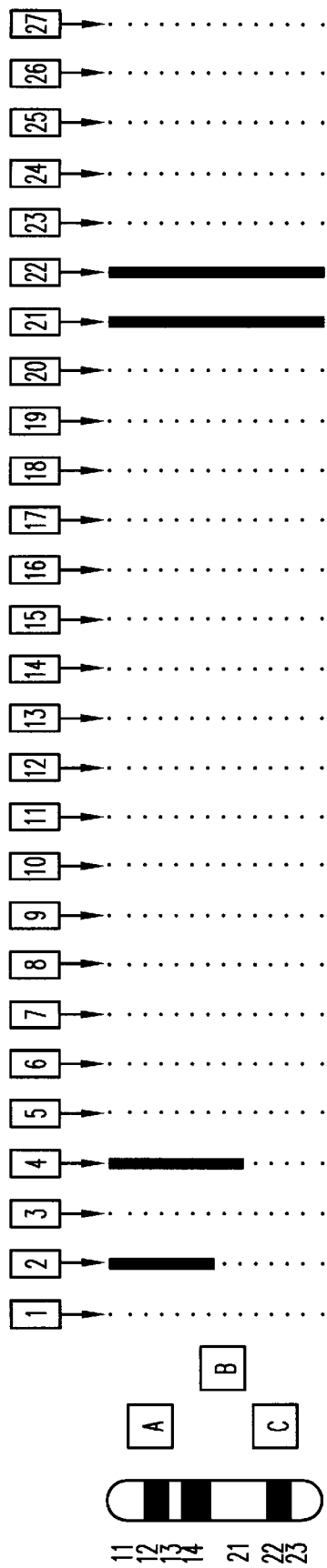

Physical mapping results were obtained with the somatic cell hybrid panel and by FISH with the YAC DNA. Strong amplification was observed in the four hybrids of the panel containing whole chromosome 17 or part of it. All the hybrids not containing this chromosome were negative (FIG. 11A). The porcine product obtained was easily distinguishable from the rodent amplification. Analysis of the results obtained on the panel localized the gene to chromosome 17q1.1–q1.4 region. Furthermore, one of the YAC containing the MTNR1A gene was labeled and hybridized on porcine metaphases. A strong fluorescent double spot was detected on pig chromosome 17 in the q1.2 region in more than 90% of the petaphases analyzed (FIG. 11B). This result is in accordance with the one obtained on the panel and allowed us to define a more accurate location of MTNR1A on chromosome 17.

Digestion of the sheep PCR product with Rsa I produced an RFLP with polymorphic alleles at 295 bp and 290 bp (FIG. 10). Three out of nine IMF reference families provided informative meioses. With this data, the two-point linkage analysis resulted in a significant linkage to ovine marker CP93 on sheep chromosome 1p (LOD=3.91). Gene frequencies of the Rsa I polymorphism in several breeds of sheep are given in Table 11.

TABLE 11

Allele frequencies of the Rsa I RFLP in breeds of sheep

| | | Frequency of each allele | |
|---|---|---|---|
| Breed | Number | 295 bp | 290 bp |
| White-faced crossbred | 36 | 0.39 | 0.61 |
| Suffolk | 18 | 0.08 | 0.92 |
| Texel | 1 | 0.00 | 1.00 |
| Coopworth | 4 | 0.00 | 1.00 |

A polymorphism was detected in the cattle fragment using Drd I. Four fragments of 394, 205, 160 and 110 bp in size separated on a 4% agarose gel. Two alleles at 394 and 205 bp segregated through the three generation bovine reference family in a pattern consistent with Mendelian inheritance (FIG. 10). The MTNR1A genotype frequencies of several breeds of cattle are given in Table 12.

TABLE 12

Genotype frequencies of the Dde I RFLP in breeds of cattle

| | | Frequency of each allele | |
|---|---|---|---|
| Breed | Number | 394 bp | 205 bp |
| Limousine | 5 | 1.00 | 0.00 |
| Simmental | 9 | 1.00 | 0.00 |
| Gelbveih | 19 | 1.00 | 0.00 |
| Holstein | 15 | 0.93 | 0.07 |
| Herford | 18 | 0.83 | 0.17 |
| Angus | 11 | 1.00 | 0.00 |
| Brahma | 3 | 0.00 | 1.00 |
| Brangus | 4 | 0.88 | 0.12 |
| REF Parents | 32 | 0.70 | 0.30 |

Results of the two-point linkage analysis of the cattle Drd I RFLP produced seven significant linkages with loci on bovine chromosome 27 (Table 10) (supra). Results of PCR experiments with the bovine somatic cell hybrid panel produced strong amplification in the panels containing bovine chromosome 27. Analysis of the results show 100% concordancy of MTNR1A to markers on BTA27 (Table 11).

TABLE 13

Concordancy Analysis of MTNR1A with Bovine Chromosome Markers

| Chromo-some | Marker | Concordant | | Discordant | | Concordancy |
|---|---|---|---|---|---|---|
| | | +/+ | −/− | +/− | −/+ | % |
| 1 | MAF46 | 8 | 7 | 5 | 11 | 48 |
| 2 | AR028 | 4 | 15 | 9 | 3 | 61 |
| 3 | BM2924 | 3 | 17 | 8 | 1 | 69 |
| 4 | TGLA159 | 4 | 14 | 9 | 4 | 58 |
| 5 | RM500 | 7 | 6 | 6 | 9 | 52 |
| 6 | BM2320 | 9 | 13 | 4 | 5 | 71 |
| 7 | ILSTS006 | 4 | 12 | 7 | 6 | 55 |
| 8 | CSSM047 | 3 | 16 | 9 | 1 | 65 |
| 9 | UWCA9 | 6 | 11 | 7 | 6 | 57 |
| 10 | CSSM038 | 9 | 12 | 3 | 6 | 70 |
| 11 | BM6445 | 6 | 13 | 7 | 5 | 61 |
| 12 | BM6116 | 6 | 13 | 7 | 5 | 61 |
| 13 | UWCA21 | 5 | 12 | 7 | 4 | 61 |
| 14 | ILSTS011 | 10 | 15 | 3 | 3 | 81 |
| 15 | BM848 | 6 | 13 | 7 | 5 | 61 |
| 16 | MYOG | 7 | 13 | 6 | 5 | 65 |

TABLE 13-continued

Concordancy Analysis of MTNR1A with Bovine Chromosome Markers

| Chromo- | | Concordant | | Discordant | | Concordancy |
|---|---|---|---|---|---|---|
| some | Marker | +/+ | -/- | +/- | -/+ | % |
| 17 | ETH185 | 9 | 15 | 4 | 3 | 77 |
| 18 | UWCA5 | 3 | 14 | 10 | 4 | 55 |
| 19 | GH | 8 | 6 | 5 | 12 | 45 |
| 20 | BM5004 | 3 | 15 | 10 | 3 | 58 |
| 21 | ETH131 | 4 | 17 | 9 | 1 | 68 |
| 22 | HRH1 | 3 | 16 | 8 | 2 | 66 |
| 23 | BoLADRB3 | 7 | 14 | 6 | 4 | 68 |
| 24 | CSSM23 | 6 | 12 | 7 | 5 | 60 |
| 25 | ELN | 5 | 11 | 7 | 7 | 53 |
| 26 | BM1314 | 5 | 14 | 7 | 4 | 63 |
| 27 | TGLA179 | 13 | 16 | 0 | 0 | 100 |
| 28 | BP23 | 7 | 10 | 6 | 8 | 55 |
| 29 | OCAM | 8 | 12 | 5 | 6 | 65 |
| X | DMD | 3 | 7 | 4 | 3 | 59 |

The addition of MTNR1A to the human and mouse genomes added another Type 1 marker to the human and mouse syntenic group which includes the genes for: plasma kallikrein (KLK3), mitochondrial uncoupling protein (UCP) and coagulation factor XI (F11) (Slaugenhaupt et al. 1995). Previous comparative mapping information has shown synteny between HSA4 and pig chromosome 8 (SSC8), with an intrachromosomal rearrangement such that the order of loci on SSC8 from SPP1 through IL2 is reversed in relation to the location of the locus PDGFRA on HSA4 (Johansson et al. 1995). The orthologous regions in the mouse are MMU3 and MMU5. While MTNR1A was distal to previously mapped genes on HSA4, it was expected that MTNR1A would map to SSC8, and it was unexpected to discover the linkage of this gene to loci on SSC17. No homology between HSA4 and SSC17 has been previously reported, even in recent chromosome painting experiments (Rettenberger et al. 1996; Fronicke et al. 1996; Goureau et al. 1996).

Several HSA4 loci have been mapped to sheep chromosome 6 (Broad et al. 1994; Lord et al. 1996) and it was expected that MTNR1A to also map to chromosome 6. A breakpoint between sheep chromosome 6 and HSA4 in the region of 4q26–27 was established by the mapping of HSA4 loci, Fibroblast growth factor 2 (FGF2, HSA4q25–27) and uncoupling protein (UCP, HSA4q28–31), to sheep chromosome 17 (Crawford et al., 1995).

In cattle, the location of MTNR1A has been shown by strong linkage to several loci on BTA27. Only recently in the bovine mapping effort has the syntenic group U25, to which MTNR1A belongs, been assigned to a cattle chromosome 27 (Gallagher et al. 1995). MTNR1A provides an additional Type I locus to this syntenic group. A comparative analysis of the bovine genome to the human and mouse genomes (Womack and Kata 1995) shows that most of HSA4 is syntenic to bovine chromosomes 6 and 17 and mouse chromosomes 3 and 5. A very small region of synteny between HSA4 and BTA27 is shown on the comparative map, anchored by the loci pseudoautosomal adenine nucleotide translocase-1 (ANT1) and F11. As in the pig, previous ZOO-FISH experiments did not detect homology between HSA4q and distal BTA27 (Solinas-Toldo et al 1995; Hayes 1995; Chowdhary et al. 1996). The size of the portion of BTA27 that is homologous to HSA4q is most likely too small for significant paint signal. There may also be something inherent in structure of chromosome termini that interferes with the probe hybridization (Hayes, 1995). The Ant1, Ucp, and Kal3 (KLK3) loci are located on mouse chromosome 8 (Ellison et al. 1996). The mapping of MTNR1A to the distal portion of BTA27 helps define the region of conserved synteny between HSA4, MMU8 and BTA27.

EXAMPLE 10 (MTNR1A)

TAQ I POLYMORPHISM AND ASSOCATION WITH LITTER SIZE

According to the invention two lines of French Large White pigs were genotyped for MTNR1A. One line was selected for hyperprolificacy while no selection was practiced on the control line. The gene frequencies are presented in Table 14 below.

TABLE 14

| | 4.3 kb Allele | 3.9 kb Allele |
|---|---|---|
| Hyperprolific line | .23 | .77 |
| Control line | .04 | .96 |

EXAMPLE 11 (RARG, MTNR1A, RBP4)

The markers herein were associated with traits according to the methods disclosed in L. Ollivier et al. 1997, Genet. Res. Camb. 68 in press, "The use of selection experiments for detecting quantitative trait loci", the disclosure of which is hereby expressly incorporated by reference.

The selection applied since 1973 on the prolificacy of French sows in order to establish a line of hyperprolific board (Legault & Gruand, 1976) provides an example for application of the methods described herein. The situation created is equivalent to a highly selected sample of individuals, the trait selected being pig litter size averaged over the first four sow parities ($\rho/h=1.66$ and SD $=3$, as given by Legault et al., 1996) and the selection intensity i=3. Two samples, of respective sizes $n_1=55$ (select) and $n_2=47$ (control), were gathered as described by Legault et al (1996). The hyperprolific and control lines were genotyped for the oestrogen receptor (ESR), retinoic acid receptor-gamma (RARG), retinol-binding protein 4 (RBP4) and melatonin receptor 1A (MTNR1A) genes by methods previously described (Rothschild et al., 1996; Messer et al., 1996 a, b, 1997). The favorable allele of ESR has been significantly associated with increased litter size in the Meishan and Large White breeds of pig (Rothschild et al., 1996).

Gene frequencies at the four loci were compared between the two samples in order to estimate $a_a$ and $a_b$ was also directly estimated on a subsample of 27 unselected sows, except for MTNR1A, due to the extremely low frequency of the favorable allele and the lack of homozygotes for that allele. The two estimates being independent, they were pooled using inverses of the sampling variances as weights. The results, given in Table 15, show that statistical significance is obtained for MTNR1A.

TABLE 15

Estimation of the effects (±SE) of four genes in pig prolificacy

| locus/allele | allele frequency in the control (q) | difference in frequency select-control ($\Delta$q) | average effect of the allele (total no. born/litter) | | |
|---|---|---|---|---|---|
| | | | $\alpha_d$[d] | $\alpha_b$[b] | estimated[c] |
| ESR/B | 0.49 | 0.06 | 0.14 ± 0.17 | 0.48 ± 0.42 | 0.19 ± 0.16NS |
| RARG/1 | 0.33 | 0.04 | 0.11 ± 0.18 | 0.14 ± 0.38 | 0.12 ± 0.17NS |
| RBP4/2 | 0.57 | 0.01 | 0.02 ± 0.17 | 0.45 ± 0.43 | 0.08 ± 0.16NS |
| MTNR1A/1 | 0.15 | 0.16 | 0.75 ± 0.24 | Not estimable | 0.75 ± 0.24** |

ESR, oestrogen receptor; RARG, retinoic acid receptor-gamma; RBP4, retinol-binding protein 4; MTNR1A, melatonin receptor 1A; $\Delta$q, $\alpha$ and $\alpha_b$ defined in text, NS, non-significant; ** P < 0.01.
[a]Sample sizes: $n_1$ = 47, $n_2$ = 55
[b]Sample size: N-27.
[c]$\alpha_d$ and $\alpha_b$ weighted by the inverses of their sampling variances (except for MTNR1A)

All references cited supra and hereinafter are expressly incorporated in their entirety by reference:

Albertsen, H. M., Abderrahim, H., Cann, H. M., Dausset, J., Le Paslier, D., Cohen, D. (1989) Construction and characterization of a yeast artificial chromosome library containing seven haploid human genome equivalents. Proc. Natl. Acad. Sci. USA 87, 4256–4260.

Archibald A., Haley C., Brown J. et al. (1995) The PiGMap consortium linkage map of the pig (Sus scrofa). Mammalian Genome 6:157–75.

Archibald, A., Haley C., Brown J., Couperwhite S., McQueen H., Nicholson D., Coppieters W., Van de Weghe A., Stratil A., Wintero A., Fredholm M., Larsen N., Nielsen V., Milan D., Woloszyn N., Robic A., Dalens M., Riquet J., Gellin J., Caritez J. C., Burgaud G., Ollivier L., Bidanel J. P., Vaiman M., Renard C., Geldermann H., Davoli R., Ruyter D., Verstege E., Groenen M., Davies W., Hoyheim B., Keiserud A., Andersson L., Ellegren H., Johansson M., Marklund L., Miller J., Anderson Dear D., Signer E., Jeffreys A., Moran C., Le Tissier P., Muladno, Rothschild M., Tuggle C., Vaske D., Helm J., Liu H. C., Rahman A., Yu T. P., Larson R. G. and Schmitz C. (1995). The PiGMap consortium linkage map of the pig (Sus scrofa). Mamm. Genome 6, 157–75.

Barendse, W., Armitage, S. M., Kossardk, L. M., Shalom, A., Kirkpatrick, B. W., Ryan, A. M., Clayton, D., Li, L., Neibergs, H. L., Zhang, N., Grosse, W. M., Weiss J., Creighton, P., McCarthy, F., Ron, M., Teale, A. J., Fries, R., McGraw, R. A. Moore, S. S., Georges, M., Soller, M., Womack, J. E., Hetzel, D. J. S. (1994). A genetic linkage map of the bovine genome. Nat. Genet. 6, 227–235.

Bishop, M. D., Kappes, S. M., Keele, J. W., Stone, R. T., Sunden, S. L. F., Hawkins, G. A., Toldo, S. S., Fries, R., Grosz, M. D., Yoo, J., Beattie, C. W. (1994). A genetic linkage map for cattle. Genetics 136, 619–639.

Broad, T. E., Burkin, D. J., Cambridge, L. M., Maher, D. W., Lewis, P. E., Ansari, H. A., Pearce, P. D., Jones, C. (1994). Seven loci on human chromosome 4 map to sheep chromosome 6: a proposal to restore the original nomenclature of this sheep chromosome. Mamm. Genome 5, 429–433.

Chowdhary, B. P., Fronicke, L., Gustavsson, I., Scherthan, H. (1996). Comparative analysis of the cattle and human genomes: detection of ZOO-FISH and gene mapping-based chromosomal homologies. Mamm. Genome 7, 297–302.

Crawford, A. M., Dodds, K. G., Ede, A. J., Pierson, C. A., Montgomery, G. W., Garmonsway, H. G., Beattie, A. E., Davies, K., Maddox, J. F., Kappes, S. M., Stone, R. T., Nguyen, T. C., Penty, J. M., Lord, E. A., Broom, J. E., Buitkamp, J., Schwaiger, W., Epplen, J. T., Matthew, P., Matthews, M. E., Hulme, D. J., Beh, K. J., McGraw, R. A., Beattie C. W. (1995). An autosomal genetic linkage map of the sheep genome. Genetics 140, 703–724.

Cybulsky, M. L.; J. W. U. Fries, A. J. Williams; P. Sultan, R. Eddy, M. Byers, T. Shows, M. A. Gimbrone, Jr. and T. Collins. Gene structure, chromosomal location, and basis for alternative mRNA splicing of the human VCAM1 gene. Proc. Nat. Acad. Sci. 88:7859–7863, 1991.

Cybulsky, M. L., M. Allan-Motamed, and T. Collins. 1993. Structure of the murine VCAM1 gene. Genomics 18:376–391.

Ebisawa, T., Karne, S., Lerner, M. R., Reppert, S. M. (1994). Expression cloning of a high affinity melatonin receptor from Xenopus dermal melanophores. Proc. Natl. Acad. Sci. USA. 91, 6133–6137.

Ellegren, H., M. Fredholm, I. Edfors-Lilja, A. K. Winter and A. Andersson. 1993. Conserved synteny between pig chromosome 8 anbd human chromosome 4 but rearranged and distorted linkage maps. Genomics 17:599–603.

Ellison, J. W., Li, X., Francke, U., Shapirao, L. J. (1996). Rapid evolution of human pseudoautosomal genes and their mouse homologs. Mamm. Genome 7, 25–30.

Eppig, J. T., Nadeau, J. H. (1995). Comparative maps: the mammalian jigsaw puzzle. Curr. Opin. Genet. Dev. 5,709–716.

Fronicke, L., Chowdhary, B. P., Scherthan, H., Gustavsson, I. (1996). A comparative map of the porcine and human genomes demonstrates ZOO-FISH and gene mapping-based chromosomal homologies. Mamm. Genome 7,285–290.

Gallagher, Jr., D. S., Ryan, A. M., Diamond, G., Bevins, C. L., Womack, J. E. (1995). Somatic cell mapping of β-defensin genes to cattle syntenic group U25 and fluorescence in sito localization to chromosome 27. Mamm. Genome 6,554–556.

Gaureau, A., Yerle, M., Schmitz, A., Riquet, J., Milan, D., Pinton, P., Frelat, G., Gellin, J. (1996). Determination of correspondences between human and porcine chromosome segments using bidirectional chromosome painting. Genomics. in press.

Green, P., Falls, K., Crooks, S. (1990). Documentation for CRIMAP, version 2.4 Washington University School of Medicine, St. Louis.

Hart T., Zhou J., Champagne C., Van Dyke T., Rao P. & Pettenati M. (1994) Assignment of the human diacylglycerol kinase gene (DAGK) to 12q13.3 using fluorescence in situ hybridization analysis. Genomics 22:246–47.

Hayes, H. (1995). Chromosome painting with human chromosome-specific DNA libraries reveals the extent and distribution of conserved segments in bovine chromosomes. Cytogenet. Cell Genet. 71, 168–174.

Helm, J. M., C. B. Schmitz, C. K. Tuggle, and M. F. Rothschild. 1994. Rapid Communication: SacI restriction fragment length polymorphism in a porcine vascular cellular adhesion molecule (VCAM1) gene. J. Anim. Sci. 72:2764.

Johansson, M., Ellegren, H., Andersson, L. (1995). Comparative mapping reveals extensive linkage conservation—but with gene order rearrangements-between the pig and human genomes. Genomics 25:682–690.

Klein, D., Moore, R., Reppert, S., eds. (1991) Suprachiasmatic Nucleus: The Mind's Clock, (New York: Oxford Press).

Krust, A., Kastner P., Petkovich M., Zelent A. & Chambon P. (1989) A third human retinoic acid receptor, hRAR-γ. Proceedings of the National Academy of Sciences of the USA 86:5310–14.

Kwee, L., H. S. Baldwin, H. M. Shen, C. L. Stewart, C. Buck, C. A. Buck, and M. A. Labow. 1995. Defective development of the embryonic and extraembryonic circulatory systems in vascular cell adhesion molecule (VCAM-1) deficient mice. Development 121:489–503.

LeSueur, Osborn, L., C. Hession, R. Tizard, C. Vasallo, S. Luhowskyj, G. Chi-Rosso, and R. Lobb. 1989. Direct expression cloning of vascular cell adhesion molecule 1, a cytokine-induced endothelial protein that binds to lymphocytes. Cell 59:1203–1211.

Lord, E. A., Lumsden, J.M., Dodds, K. G., Henry, H. M., Crawford, A. M., Ansari, H. A., Pearce, P. D., Maher, D. W., Stone, R. T., Kappes, S. M., Beattie, C. W., Montgomery, G. W. (1996). The linkage map of sheep chromosome 6 compared with orthologous regions in other species. Mamm. Genome 7, 373–376.

Mattei M., Riviere M., Krust A. et al. (1991) Chromosomal assignment of retinoic acid receptor (RAR) genes in the human, mouse, and rat genomes. Genomics 10:1061–69.

Montgomery, G. W., Crawford, A. M., Penty, J. M., dodds, K. G., Ede, A. J., Henry, H. M., Pierson, C. A., Lord, E. A., Galloway, S. M., Schmack, A. E., Sise, J. A., Swarbrick, P. A., Hanrahan, V., Buchanan, F. C., Hill, D. F. (1993). The ovine Booroola fecundity gene (Fec$^B$) is linked to markers from a region of human chromosome 4q. Nature Genet. 4, 410–414.

Nunes, M., Peelman, L., Vaiman, M., Bourgeaux, N., Chardon, P. (1994). Characterization of six new loci within the swine major histocompatibility complex class III region. Mammal. Genome 5, 616–622.

O'Brien, S. J., Womack, J. E., Lyons, L. A., Moore, K. J., Jenkins, N. A., Copeland, N. G. (1993). Anchored reference loci for comparative genome mapping in mammals. Nature Genet. 3, 103–112.

O'Brien, S. J., Peters, J., Searle, A., Womack, J., Marshall-Graves, J. (1993). Report of the committee on comparative gene mapping. Genome Priority Reports 1, 758–809.

Reppert, S. M., Weaver, D. R., Ebisawa, T. (1994). Cloning and characterization of a mammalian melatonin receptor that mediates reproductive and circadian responses. Neuron 13, 1177–1185.

Reppert, S. M., Godson, C., Mahle, C. D., Weaver, D. R., Slaugenhaupt, S. A., Gusella, J. F. (1995). Molecular characterization of a second melatonin receptor expressed in human retina and brain: the $Mel_{1-b}$ melatonin receptor. Proc. Natl. Acad. Sci. USA 92, 8734–8738.

Rettenberger, G., Fries, R., Engel, W., Scheit, K. H., Dolf, G., Hameister, H. (1994). Establishment of a partially informative porcine somatic cell hybrid panel and assignment of the loci for transition protein 2 (TNP2) and protamine 1 (PRM1) to chromosome 3 and polyubiquitin (UBC) to chromosome 14. Genomics 21, 558–566.

Rettenberger, G., Klett, C., Zechner, U., Kunz, J., Vogel, W., Hameister, H. (1995). Visualization of the conservation of synteny between humans and pigs by heterologous chromosomal painting. Genomics 26, 372–378.

Rettenberger, G., Bruch, J., Fries, R., Archibald, A. L., Hameister, H. (1996). Assignment of 19 porcine type I loci by somatic cell hybrid analysis detects new regions of conserved synteny between human and pig. Mamm. Genome 7, 275–279.

Robic, A., Riquet, J., Yerle, M., Milan, D., Lahbib-Mansais, Y., Dubut-Fontana, C., Gellin, J. (1996). Porcine if linkage and cytogenetic maps integrated by regional mapping of 100 microsatellites on somatic cell hybrid panel. Mamm. Genome 7, 438–445.

Rogel-Gaillard, C, Bourgeaux, N., Save, J. C., Renard, C., Coullin, P., Yerle, M., Vaiman, M., Chardon, P. (1997) Construction of a Swine YAC library allowing an efficient recovery of unique and centromeric repeated sequences. Mamm. Genome 8, 186–192.

Rohrer, G. A., Alexander, L. J., Keele, J. W., Smith, T. P., Beattie, C. W. (1994). A microsatellite linkage map of the porcine genome. Genetics 136:231–245.

Rothschild, M. F., C. Jacobson, D. A. Vaske, C. K. Tuggle, T. H. Shorr, S.Sa(aki, G. R. Erchardt, and D. G. McLaren. (1994). A major gene for litter size. Proceedings of the 5th World Congress on Genetics Applied to Livestock Production, Guelph, Canada.

Rothschild, M. F. et al. (1996) Proc. Natl. Acad. Sci. USA 93:201–5.

Slaugenhaupt, S. A., Roca, A. L., Liebert, C. B., Altherr, M. R., Gusella, J. F., Reppert, S. M. (1995). Mapping of the gene for the $Me_{1a}$-melatonin receptor to human chromosome 4 (MTNR1A) and mouse chromosome 8 (Mtnr1a). Genomics 27, 355–357.

Solinas-Toldo-S., Lengauer, C., Fries, R. (1995). Comparative genome map of human and cattle. Genomics 27, 489–496.

Tedder T. F., D. A. Steeber, and A. Chen. 1995. The Selectins: vascular adhesion molecules. FASEB J. 9:866–973.

Trent, J., Olson S. & Lawn R. (1982) Chromosomal localization of human leukocyte, fibroblast, and immune interferon genes by means of in situ hybridization. Proceedings of the National Academy of Sciences of the USA 79:7809–13.

Weaver, D. R., Rivkees, S. A., Carlson, L. L., Reppert, S. M. (1991). Localization of melatonin receptors in mammalian brain. In Suprachiasmatic Nucleus: The Mind's Clock, D. Klein, R. Moore, and S. Reppert, eds. (New York: Oxford Press). pp. 289–308.

Womack, J. E., Moll, Y. D. (1986). Gene map of the cow: conservation with mouse and man. J. Hered. 77, 2–7.

Womack, J. E., Bolch, S. N., Fries, R. (1993). Gene map of the cow (Bos taurus) 2n=60; In Genetic Maps, Vol 7, S. J. O'Brien, ed. (Cold Spring Harbor, N.Y.: Cold Spring Harbor Laboratory Press) pp. 4264–4275.

Womack, J. E., Kata, S. R. (1995). Bovine genome mapping: evolutionary inference and the power of comparative genomics. Curr. Opin. Genet. Dev. 5, 725–733.

Yerle, M., Goureau, A., Gellin, J., Le Tissier, P., Moran, C. (1994). Rapid mapping of cosmid clones on pig chromosomes by fluorescence in situ hybridization. Mamm. Genome 5, 34–37.

Yearle, M., Echard, G., Robic, A., Mairal, A., Dubut-Fontana, C., Riquet, J., Pinton, P., Milan, D., Lahbib-Mansais, Y., Gellin, J. (1996). A somatic cell hybrid panel for pig regional gene mapping characterized by molecular cytogenetics. Cytogenet. Cell Genet. in press.

Yelich, J., Pomp D. & Geisert R. (1995) Retinoic acid receptor, retinol binding protein, transforming growth factor-β and aromatase gene expression during rapid trophoblastic elongation. Biology of Reproduction 52: (Suppl.1), 179.

Zelent A., Krust A., Petkovich M., Kastner P. & Chambon P. (1989) Cloning of murine α and β retinoic acid receptors and a novel receptor γ predomianantly expressed in skin. Nature 339:714–17.

Zhang, N., Threadgill, D. W., Womack, J. E. (1992). Synteny mapping in the bovine: genes from human chromosome 4. Genomics 14, 131–136.

What is claimed is:

1. A method of screening animals to determine those more likely to exhibit favorable reproductive traits of increased litter size or higher weaning weight comprising:

obtaining a sample of genetic material from an animal; and assaying for the presence of a polymorphism in a reproductive gene in said sample said polymorphism associated with increased litter size or higher weaning weight, said reproductive gene selected from the group consisting of: retinol binding protein 4; retinoic acid receptor gamma; melatonin receptor 1a; and vascular adhesion molecule 1.

2. The method of claim 1 wherein said animal is a pig.

3. The method of claim 1 wherein the step of assaying is selected from the group consisting of: direct sequence analysis, restriction fragment length polymorphism (RFLP) analysis, heteroduplex analysis, single strand conformational polymorphism (SSCP), denaturing gradient gel electrophoresis (DGGE) and temperature gradient gel electrophoresis (TGGE).

4. The method of claim 1 wherein the step of assaying for the presence of said polymorphism comprises the steps of:

digesting said genetic material with a restriction enzyme that cleaves said reproductive gene in at least one place;

separating the fragments obtained from the digestion;

detecting a restriction pattern generated by said fragments; and comparing said pattern with a second restriction pattern for the reproductive gene obtained by using said restriction enzyme, wherein said second restriction pattern is associated with increased litter size.

5. The method of claim 3 wherein the separation is by gel electrophoresis.

6. The method of claim 3 wherein the step of comparing said restriction patterns comprises identifying specific fragments by size and comparing the sizes of said fragments.

7. The method of claim 6 wherein the step of detecting different sizes of the fragments comprises the steps of:

separating said fragments by size using gel electrophoresis in the presence of a control DNA fragment of known size;

contacting said separated fragments with a probe that hybridizes with said fragments to form probe fragment complexes; and determining the size of separated fragments by detecting the presence of the probe fragment complexes and determining their relative positions with respect to said control DNA fragment.

8. The method of claim 4 further comprising the step of amplifying the amount of said reproductive gene or a portion thereof which contains said polymorphism, prior to said digestion step.

9. The method of claim 8 wherein said amplification is conducted with Taq polymerase.

10. The method of claim 8 wherein said amplification includes the steps of:

selecting a forward and a reverse sequence primer capable of amplifying a region of said reproductive gene which contains a polymorphic site.

11. The method of claim 10 wherein said gene is the retinoic acid receptor gamma gene and said forward and reverse primers are selected from and based upon the sequence disclosed in FIG. 8 which is SEQ ID NO. 5.

12. The method of claim 11 wherein said primers are SEQ ID NO:16 and SEQ ID NO:17.

13. The method of claim 12 wherein said restriction enzyme is Stu I.

14. The method of claim 13 wherein said polymorphism is a 5.0 kb restriction length polymorphism.

15. The method of claim 13 wherein said polymorphism is a 3.2+1.8 restriction length polymorphism.

16. The method of claim 1 wherein said gene is retinoic acid receptor gamma and said reproductive trait is increased litter size.

Figure 6:
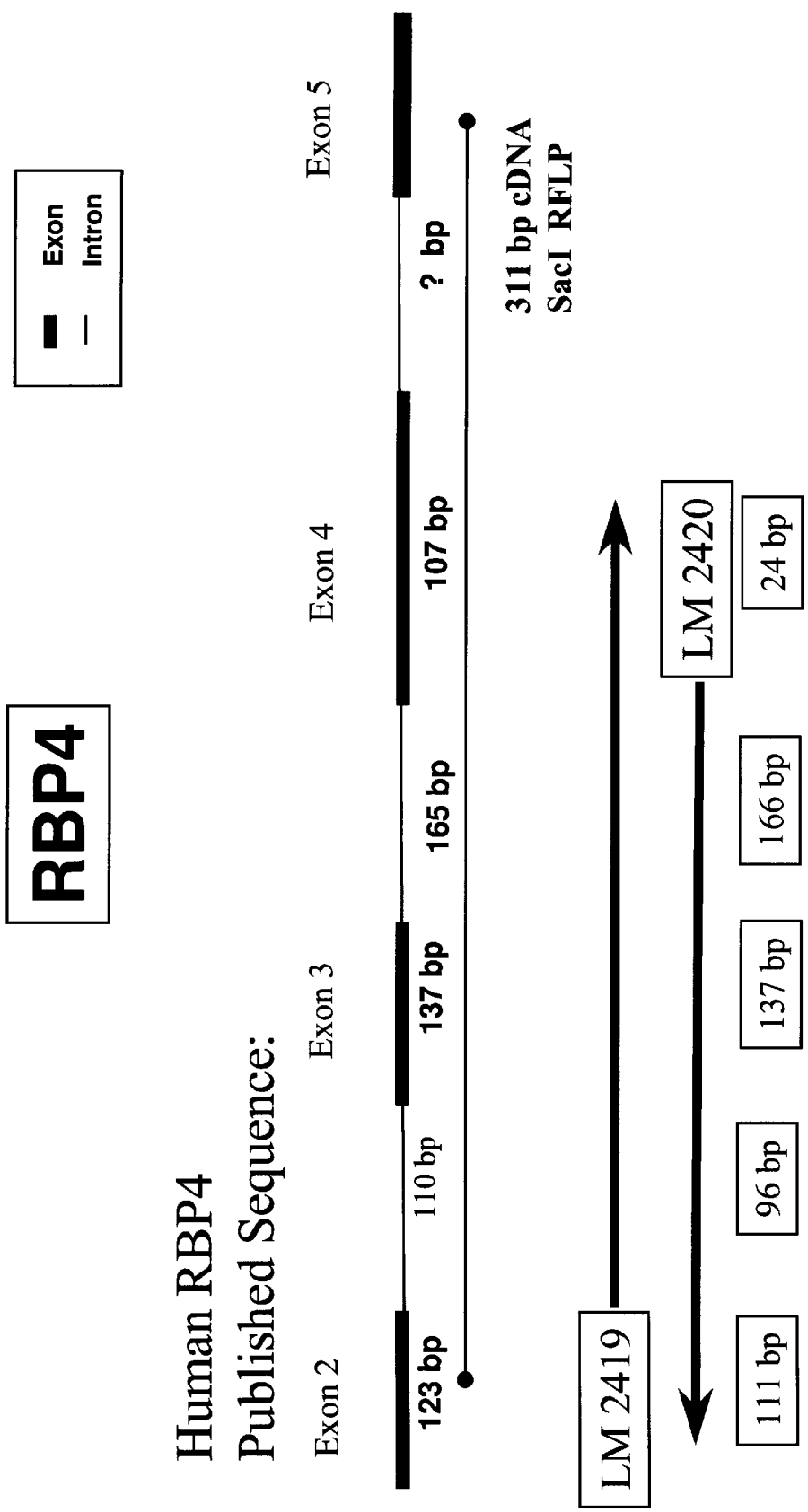
FIG. 6 is a schematic depicting a comparison of the human published retinol binding protein 4 sequence and the new pig retinol binding protein 4 sequence.
Figure 7:
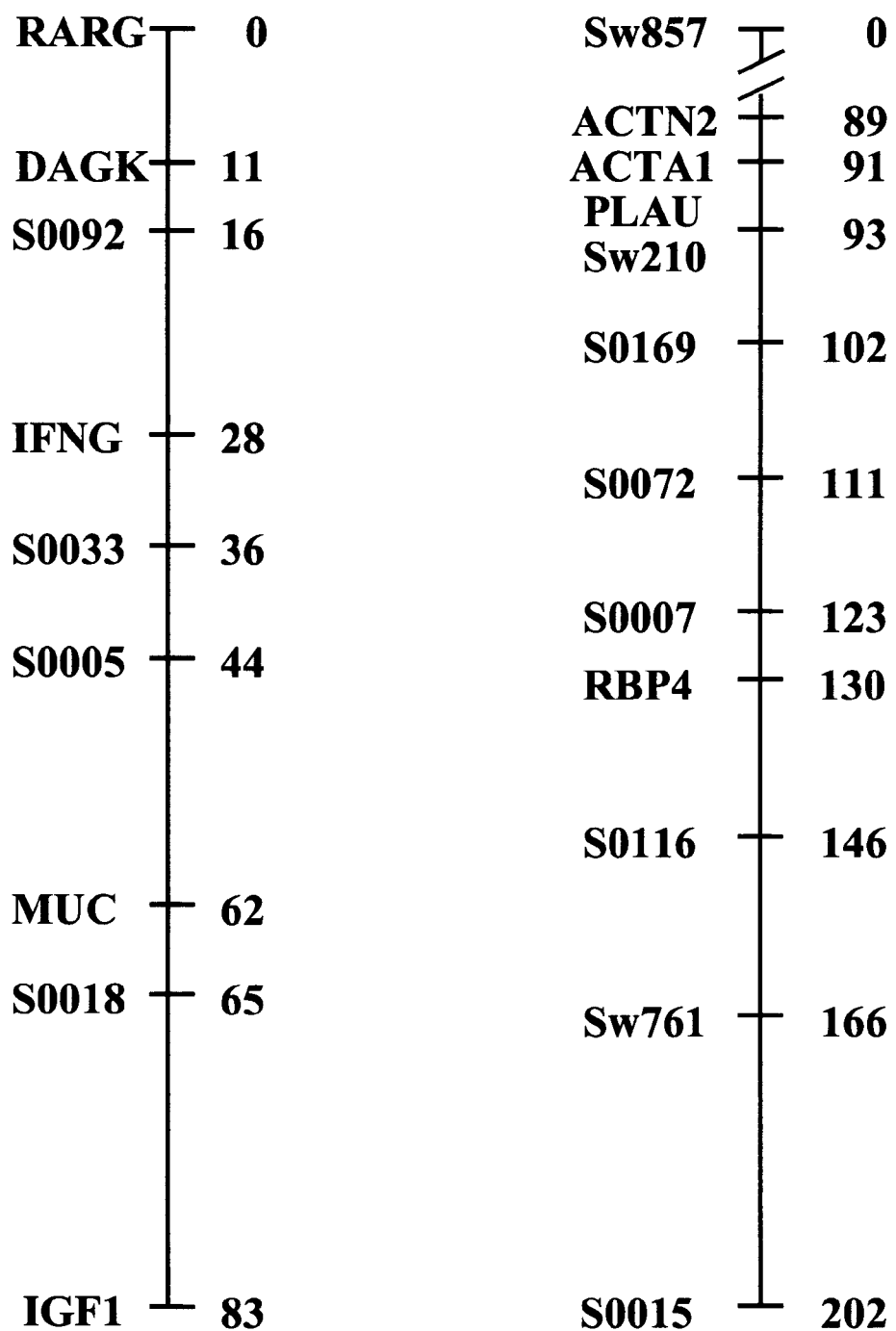
FIG. 7 is a linkage map of SSC 5 (on the left) and a partial linkage map of SSC 14 (on the right). Distances are in Kosambi cM.

17. The method of claim 10 wherein said gene is the retinol binding protein 4 and said forward and reverse primers are selected from and based upon the sequence disclosed in FIG. 6.

18. The method of claim 17 wherein said primers are SEQ ID NO:14 and SEQ ID NO:15.

19. The method of claim 17 wherein said primers are SEQ ID NO:18 and SEQ ID NO:19.

20. The method of claim 19 wherein said restriction enzyme is Msp I.

21. The method of claim 20 wherein said polymorphism is a 190 bp restriction length polymorphism.

22. The method of claim 20 wherein said polymorphism is a 125 bp restriction length polymorphism.

23. The method of claim 1 wherein said gene is retinol binding protein 4 and said reproductive trait is increased litter size.

24. The method of claim 10 wherein said gene is melatonin receptor 1a.

25. The method of claim 24 wherein said primers are SEQ ID NO:22 and SEQ ID NO:23.

26. The method of claim 25 wherein said restriction enzyme is Taq I.

27. The method of claim 26 wherein said polymorphism is a 4.3 kbp restriction length polymorphism.

28. The method of claim 26 wherein said polymorphism is a 3.9 kbp restriction length polymorphism.

29. The method of claim 1 wherein said gene melatonin receptor 1a and said reproductive trait is increased litter size.

30. A method of screening animals to determine those more likely to exhibit favorable reproductive traits such as increased litter size or higher weaning weight comprising:

obtaining a sample of genetic material from an animal; and assaying for the presence of a polymorphism in a reproductive gene in said sample, said polymorphism associated with increased litter size or higher weaning weight, said reproductive gene being vascular adhesion molecule 1;

wherein said assaying for the presence of said polymorphism comprises the steps of:

amplifying the amount of said reproductive gene or a portion thereof which contains said polymorphism by selecting a forward and reverse sequence primer capable of amplifying the 3' untranslated region of said gene;

digesting said genetic material with a restriction enzyme that cleaves said reproductive gene in at least one place;

separating the fragments obtained from said digestion;

detecting a restriction pattern generated by said fragments; and;

comparing said pattern with a second restriction enzyme, wherein said second restriction pattern is associated with increased litter size.

31. The method of claim 30 wherein said primers are SEQ ID NO:10 and SEQ ID NO:11.

32. The method of claim 30 wherein primers are SEQ ID NO:12 and SEQ ID NO:13.

33. The method of claim 30 wherein said restriction enzyme is Taq I.

34. The method of claim 30 wherein said polymorphism is allele A1 as shown in the sequence in FIG. 3 which is SEQ ID NO:1.

35. The method of claim 30 wherein said polymorphism is allele A2 as shown in the sequence in FIG. 3 which is SEQ ID NO:2.

36. The method of claim 30 wherein said polymorphism allele B as shown in the sequence in FIG. 3 which is SEQ ID NO:3.

37. The method of claim 30 wherein said polymorphism allele C as shown in the sequence in FIG. 3 which is SEQ ID NO:4.

38. The method of claim 34 or 35 wherein said allele is associated with increased litter size.

39. The method of claim 34 or 35 wherein said allele is associated with low weaning weight.

40. The method of claim 37 wherein said polymorphism is allele c and said allele is low weaning weight.

41. A method for screening pigs to determine those more likely to produce larger litters, and/or those less likely to produce smaller litters, which method comprises of the steps of:

determining an allele of a reproductive gene present in an animal;

determining an allele of other markers for genes known to affect litter size; and selecting for animals with favorable combinations of alleles and against those carrying unfavorable combinations.

42. The method of claim 42 wherein said reproductive gene is selected from the group consisting of: retinol binding protein 4; retinoic acid receptor gamma; melatonin receptor 1a; and vascular adhesion molecule 1.

43. The method of claim 42 wherein the determination of reproductive gene alleles comprises: determining the presence of at least one allele associated with at least one DNA marker linked either directly or indirectly to said reproductive gene.

44. The method as claimed in claim 42 wherein the DNA marker is a microsatellite.

45. A method of screening animals to determine those more likely to have larger litters or higher weaning weight comprising:

obtaining a sample of genetic material from said animal; and assaying for the presence of a polymorphism in the vascular adhesion molecule 1 gene said polymorphism being one which is identifiable by alleles A1 and A2, B or C as depicted in FIG. 3.

46. A method of screening animals to determine those more likely to have larger litters comprising:

obtaining a sample of genetic material from said animal; and assaying for the presence of a polymorphism in the retinoic acid receptor gamma gene, said polymorphism being one which is identifiable by the presence or absence of a Stu I polymorphism in the region amplified by the primers SEQ ID NO:16 and SEQ ID NO:17.

47. A method of screening animals to determine those more likely to have larger litters comprising:

obtaining a sample of genetic material from said animal; and assaying for the presence of a polymorphism in the retinol binding protein 4 gene said polymorphism being one which is identifiable by the presence or absence of a Msp I polymorphism in the region amplified by the primers SEQ ID NO:18 and SEQ ID NO:19.

48. A method of screening animals to determine those more likely to have larger litters comprising:

obtaining a sample of genetic material from said animal; and assaying for the presence of a polymorphism in the melatonin receptor 1 gene, said polymorphism being one which is identifiable by the presence or absence of a Taq I site in the region amplified by primers SEQ ID NO:22 and SEQ ID NO:23.

49. A method of screening animals to identify polymorphic markers linked to specific reproductive genes which are associated with altered litter size or weaning weight comprising:

selecting nucleic acid sequences linked to reproductive genes selected from the group consisting of RPB4, RARG, melatonin receptor 1 and VCAM1;

obtaining nucleic acid from individual animals differing in their breeding value for reproductive traits;

assaying for polymorphisms in said genes; and associating such polymorphisms with high or low breeding value.

* * * * *

UNITED STATES PATENT AND TRADEMARK OFFICE
CERTIFICATE OF CORRECTION

PATENT NO. : 5,939,264
DATED : August 17, 1999
INVENTOR(S) : Max F. Rothschild; Christopher K. Tuggle; Lori A. Messer; Tun-Ping Yu It is certified that error appears in the above-identified patent and that said Letters Patent is hereby corrected as shown below:

Column 4, line 50 delete [SEQ ID NO:10] and substitute --SEQ ID NO:9--.

Column 5, line 11 delete [litteranimals. It provides a meanimals.] and substitute --litter size in pigs and other animals.--

Column 19, line 33 delete [Sacd] and substitute --SacI--.

Column 19, line 45 delete [Sac1] and substitute --SacI--.

Column 21, line 60 delete [HTMR1A] and substitute --MTNR1A--.

Column 22, line 45 delete [MgCM$_2$] and substitute --MgC1$_2$--.

UNITED STATES PATENT AND TRADEMARK OFFICE
CERTIFICATE OF CORRECTION

PATENT NO. : 5,939,264
DATED : August 17, 1999
INVENTOR(S) : Max F. Rothschild; Christopher K. Tuggle; Lori A. Messer; Tun-Ping Yu It is certified that error appears in the above-identified patent and that said Letters Patent is hereby corrected as shown below:

Column 33 through Column 65, line 19, Substitute Sequence Listing with attached. Format has to be exactly as submitted.

Claim 42, column 68, line 1, delete [42] and substitute --41--.

Signed and Sealed this

Third Day of October, 2000

*Attest:*

*Attesting Officer*

Q. TODD DICKINSON

*Director of Patents and Trademarks*

SEQUENCE LISTING (1) GENERAL INFORMATION:

(iii) NUMBER OF SEQUENCES: 25

(2) INFORMATION FOR SEQ ID NO:1:

(i) SEQUENCE CHARACTERISTICS:
      (A) LENGTH: 457 base pairs
      (B) TYPE: nucleic acid
      (C) STRANDEDNESS: single
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Sus scrofa
      (F) TISSUE TYPE: Vascular cambium (viii) POSITION IN GENOME:
      (A) CHROMOSOME/SEGMENT: VCAM A1

(xi) SEQUENCE DESCRIPTION: SEQ ID NO:1:

```
AAATGCAGTG AACTCTTGGA AAGACATGGC TGCCTATGCC CTTGCGGTGT GCACGAAGCC        60

AAAGGAAAAC GGCTTTCTCA AAAATAGGCA CTACCCCTGA GATATGGTGA CTGGGGTGGT      120

GTCATGAAGT GTATGTACAA TAACGTGATT TGTATATATG TAAAATAAAA TTATGCCATA      180

GGAAGATCGC CTGGAATATC AGCCCTCCAT AGTCACATTT CTAAAATTAT CAGTGTTGCT      240

TGGACTGATC GTTATAACTT AATGCATCTT AATATGACTG GCACTTTTTA ATATTTTATG      300

TCATCTTTTT AATATTTTGT TACGACTTTT CAATATTTTA TTCCTTTTAA CAATATTTGA      360

TTCCTATACA GGTCATGGAC AACAATTTCA TGTTTTGTAA AGATGCCAGG GTTTTAGATT      420

GTTACAGGCA AATGATAAAC CAAGAAAGAA CTGGGTT                               457
```

(2) INFORMATION FOR SEQ ID NO:2:

```
        (i) SEQUENCE CHARACTERISTICS:
            (A) LENGTH: 457 base
pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Sus scrof
a
             (F) TISSUE TYPE: Vascul
ar cambium (viii) POSITION IN GENOME:
             (A) CHROMOSOME/SEGMENT: VC
AM A2

(xi) SEQUENCE DESCRIPTION: SEQ ID NO:2:

AAATGCAGTG AACTCTTGGA AAGACATGGC TGCCTATGCC CTTGCGGTGT GC
ACGAAGCC        60

AAAGGAAAAC GGCTTTCTCA AAAATAGGCA CTACCCCTGA GATATGGTGA CT
GGGGTGGT       120

GTCATGAAGT GTATGTACAA TAACGTGATT TGTATATATG TAAAATAAAA TT
ATGCCATA       180

GGAAGATCGC CTGCAATATC AGCCCTCCAT AGTCACATTT CTAAAATTAT CA
GTGTTGCT       240

TGGACTGATC GTTATAACTT AATGCATCTT AATATGACTG GCACTTTTTA AT
ATTTTATG       300

TCATCTTTTT AATATTTTGT TACGACTTTT CAATATTTTA TTCCTTTTAA CA
ATATTTGA       360

TTCCTATACA GGTCATGGAC AACAATTTCA TGTTTTGTAA AGATGCCAGG GT
TTTAGATT       420

GTTACAGGCA AATGATAAAC CAAGAAAGAA CTGGGTT
    457

(2) INFORMATION FOR SEQ ID NO:3:

(i) SEQUENCE CHARACTERISTICS:
            (A) LENGTH: 457 base
pairs
            (B) TYPE: nucleic acid
            (C) STRANDEDNESS: single
            (D) TOPOLOGY: linear (ii) MOLECULE TYPE: DNA (genomic)

(iii) HYPOTHETICAL: NO (iv) ANTI-SENSE: NO (vi) ORIGINAL SOURCE:
             (A) ORGANISM: Sus scrof
a
             (F) TISSUE TYPE: Vascul
ar cambium (viii) POSITION IN GENOME:
             (A) CHROMOSOME/SEGMENT: VC
AM B (xi) SEQUENCE DESCRIPTION: SEQ ID NO:3:

AAATGCAGTG AACTCTTGGA AAGACATGGC TGCCTATGCC CTTGCGGTGT GC
ACGAAGCC        60
```

```
AAAGGAAAAC GGCTTTCTCA AAAATAGGCA CTACCCCTGA GATATGGTGA CT
GGGGTGGT    120

GTCATGAAGT GTATGTACAA TAACGTGATT TGTATATATG TAAAATAAAA TT
ATGCCATA    180

GGAAGATCGC CTGCAATATC AGCCCTCCAT AGTCACATTT CTAAAATTAT CA
GTGTTGCT    240

TGGACTGATC GTTATAACTT AATGCATCTT AATATGACTG GCACTTTTTA AT
ATTTTATG    300

TCATCTTTTT AATATTTTGT TACGACTTTT CAATATTTTA TTTCCTTTAA CA
ATATTTGA    360

TTCCTATAAA GGTCATGGAC AACAATTTCA TGTTTTGTAA AGATGCCAGG GT
TTTAGATT    420

GTTACAGGCA AATGATAAAC CAAGAAAGAA CTGGGTT
        457
```

(2) INFORMATION FOR SEQ ID NO:4:

(i) SEQUENCE CHARACTERISTICS:
        (A) LENGTH: 463 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Sus scrofa
        (F) TISSUE TYPE: Vascular cambium (viii) POSITION IN GENOME:
        (A) CHROMOSOME/SEGMENT: VCAM C (xi) SEQUENCE DESCRIPTION: SEQ ID NO:4:

```
AAATGCAGTG AACTCTTGGA AAGACATGGC TGCCTATGCC CTTGCGGTGC GC
ATGAAGCC    60

AAAGGAAAAC GGCTTTCTCA AAAATAGGCA CTACCCCTGA GATATAGTGA CT
GGGGTGGT    120

GTCATGAAGT GTATGTACAA TAATGTGATT TGTATATATG TAAAATAAAA TT
ATGCCATA    180

GGAAGATCTC CTGGAATATC AGCCCTCCAT AGTCACATTT CTAAAATTAT CA
AAGTGTTG    240

CTTGGACTGA TCGTTATAAC TTAATGCATC TTAATATCGA CTGGCACTTT TT
AATATTTT    300

ATGTCATCTT TTTAATATTT TGTTATGACT TTTCAATATT TTATTTCCTT TA
ACAATATT    360

TGATTCCTAT AAAGGTCATG GACAACAATT TCATGTTTTG TAAAGATGCC AG
GGTTTTAG    420

ATTGTTACAG GCAAATAACA ATAAACCAAG AAAGAACTGG GTT
463
```

(2) INFORMATION FOR SEQ ID NO:5:

(i) SEQUENCE CHARACTERISTICS:

(A) LENGTH: 558 base pairs
(B) TYPE: nucleic acid
(C) STRANDEDNESS: single
(D) TOPOLOGY: linear (ii) MOLECULE TYPE: cDNA (iii) HYPOTHETICAL: NO (iv) ANTI-SENSE: NO (vi) ORIGINAL SOURCE:
(C) INDIVIDUAL ISOLATE: Porcine embryo RARG
(D) DEVELOPMENTAL STAGE: Embryo
(F) TISSUE TYPE: Embryo (xi) SEQUENCE DESCRIPTION: SEQ ID NO:5:

```
AACTGAGCCC CCAGTTAGAA GAGCTCATCA CCAAGGTCAG CAAAGTCCAT CA
AGAGACGC       60

TCCTCCCCGC TCTGCCAGCT GGGCAATTAC ACCACGAACT CCAGTGTAGA CC
ACCGTGTG       120

CAGCTGGATC TGGGGCTGTG GGACCAAGTT CAGTGAGCTG GTCACCAAGT GC
ATCATTAA       180

GATCGCGGAG NTTGTCAAGC GGCTGTCCTG TTTTACAGGG CTCCAGTATT GC
TGACCAGA       240

TCACTCTGCT CAAGGCTGCC TGCCTGGACA TCCTGATGCT GCGGNTCTGC AC
AAGGTCCA       300

CCCCCGGCGC AGNCTATCAT GCACCTCTCT GATGGGCTGA CCCTGAACCG GA
NCCAGATG       360

CACGATGCTG ACTTCGGGCC CCCTCACAGA CNTCGTCTGT GCCTTTGCTG GG
CAGCTCCT       420

GCCACTGGAG ATGGATGACA CAGAGACAGG GCTGCTCAGC CGCCATCTGC CT
CATCTGCG       480

GAGACCGCAT GGACCTGGAG GAACCCGAGT AAGTGGACAA GCTGCAGGAG CC
ATTGCTGG       540

AAGCCCTGAG GCTCTATG

558
```

(2) INFORMATION FOR SEQ ID NO:6:

(i) SEQUENCE CHARACTERISTICS:
(A) LENGTH: 353 amino acids
(B) TYPE: amino acid
(C) STRANDEDNESS:
(D) TOPOLOGY: unknown (ii) MOLECULE TYPE: peptide (iii) HYPOTHETICAL: NO (iv) ANTI-SENSE: NO (vi) ORIGINAL SOURCE:
(A) ORGANISM: Homo sapiens
(G) CELL TYPE: Melanocyte
(H) CELL LINE: human melatonin receptor 1a (viii) POSITION IN GENOME:
(B) MAP POSITION: 14

(xi) SEQUENCE DESCRIPTION: SEQ ID NO:6:

Met Gln Gly Asn Gly Ser Ala Leu Pro Asn Ala Ser Gln Pro Val Leu
1               5                  10                  15

Arg Gly Asp Gly Ala Xaa Xaa Xaa Arg Pro Ser Trp Leu Ala Ser Ala
            20                  25                  30

Leu Ala Cys Val Leu Ile Phe Thr Ile Val Val Asp Ile Leu Gly Asn
        35                  40                  45

Leu Leu Val Ile Leu Ser Val Tyr Arg Asn Lys Lys Leu Arg Asn Ala
    50                  55                  60

Gly Asn Ile Phe Val Val Ser Leu Ala Val Ala Asp Leu Val Val Ala
65                  70                  75                  80

Ile Tyr Pro Tyr Pro Leu Val Leu Met Ser Ile Phe Asn Asn Gly Trp
                85                  90                  95

Asn Leu Gly Tyr Leu His Cys Gln Val Ser Gly Phe Leu Met Gly Leu
            100                 105                 110

Ser Val Ile Gly Ser Ile Phe Asn Ile Thr Gly Ile Ala Ile Asn Arg
        115                 120                 125

Tyr Cys Tyr Ile Cys His Ser Leu Lys Tyr Asp Lys Leu Tyr Ser Ser
    130                 135                 140

Lys Asn Ser Leu Cys Tyr Val Leu Leu Ile Trp Leu Leu Thr Leu Ala
145                 150                 155                 160

Ala Val Leu Pro Asn Leu Arg Ala Gly Thr Leu Gln Tyr Asp Pro Arg
                165                 170                 175

Ile Tyr Ser Cys Thr Phe Ala Gln Ser Val Ser Ser Ala Tyr Thr Ile
            180                 185                 190

Ala Val Val Val Phe His Phe Leu Val Pro Met Ile Ile Val Ile Phe
        195                 200

```
            205

Cys Tyr Leu Arg Ile Trp Ile Leu Val Leu Gl
n Val Arg Gln Arg Val
    210
    215
    220

Lys Pro Asp Arg Lys Pro Lys Leu Lys Pro Gl
n Asp Phe Arg Asn Phe
225                  2
30           2
35                2
40

Val Thr Met Phe Val Val Phe Val Leu Phe Al
a Ile Cys Trp Ala Pro
            245
            250
            255

Leu Asn Phe Ile Gly Leu Ala Val Ala Ser As
p Pro Ala Ser Met Val
            260
            265
            270

Pro Arg Ile Pro Glu Trp Leu Phe Val Ala Se
r Tyr Tyr Met Ala Tyr
        275
        280
        285

Phe Asn Ser Cys Leu Asn Ala Ile Ile Tyr Gl
y Leu Leu Asn Gln Asn
    290
    295
    300

Phe Arg Lys Glu Tyr Arg Arg Ile Ile Val Se
r Leu Cys Thr Ala Arg
305                  3
10           3
15                3
20

Val Phe Phe Val Asp Ser Ser Asn Asp Val Al
a Asp Arg Val Lys Trp
            325
            330
            335

Lys Pro Ser Pro Leu Met Thr Asn Asn Asn Va
l Val Lys Val Asp Ser
            340
            345
            350

Val (2) INFORMATION FOR SEQ ID NO:7:

(i) SEQUENCE CHARACTERISTICS:
        (A) LENGTH: 366 amino
acids
        (B) TYPE: amino acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Ovis ammo
n aries
        (G) CELL TYPE: Melanocy
``` te (xi) SEQUENCE DESCRIPTION: SEQ ID NO:7:

```
Met Ala Gly Arg Leu Trp Gly Ser Pro Gly Gly Thr Pro Lys Gly Asn
1               5                  10                  15

Gly Ser Ser Ala Leu Leu Asn Val Ser Gln Ala Ala Pro Gly Ala Gly
                20                  25                  30

Asp Gly Val Arg Pro Arg Pro Ser Trp Leu Ala Ala Thr Leu Ala Ser
            35                  40                  45

Ile Leu Ile Phe Thr Ile Val Val Asp Ile Val Gly Asn Leu Leu Val
        50                  55                  60

Val Leu Ser Val Tyr Arg Asn Lys Lys Leu Arg Asn Ala Gly Asn Val
65                  70                  75                  80

Phe Val Val Ser Leu Ala Val Ala Asp Leu Leu Val Ala Val Tyr Pro
                85                  90                  95

Tyr Pro Leu Ala Leu Ala Ser Ile Val Asn Asn Gly Trp Ser Leu Ser
                100                 105                 110

Ser Leu His Cys Gln Leu Ser Gly Phe Leu Met Gly Leu Ser Val Ile
            115                 120                 125

Gly Ser Val Phe Ser Ile Thr Gly Ile Ala Ile Asn Arg Tyr Cys Cys
        130                 135                 140

Ile Cys His Ser Leu Arg Tyr Gly Lys Leu Tyr Ser Gly Thr Asn Ser
145                 150                 155                 160

Leu Cys Tyr Val Phe Leu Ile Trp Thr Leu Thr Leu Val Ala Ile Val
                165                 170                 175

Pro Asn Leu Cys Val Gly Thr Leu Gln Tyr Asp Pro Arg Ile Tyr Ser
                180                 185                 190

Cys Thr Phe Thr Gln Ser Val Ser Ser Ala Tyr Thr Ile Ala Val Val
```

```
            195
            200
            205

Val Phe His Phe Ile Val Pro Met Leu Val Va
l Val Phe Cys Tyr Leu
    210
    215
    220

Arg Ile Trp Ala Leu Val Leu Gln Val Arg Tr
p Lys Val Lys Pro Asp
225                         2
30                          2
35                          2
40

Asn Lys Pro Lys Leu Lys Pro Gln Asp Phe Ar
g Asn Phe Val Thr Met
            245
            250
            255

Phe Val Val Phe Val Leu Phe Ala Ile Cys Tr
p Ala Pro Leu Asn Phe
            260
            265
            270

Ile Gly Leu Val Val Ala Ser Asp Pro Ala Se
r Met Ala Pro Arg Ile
        275
        280
        285

Pro Glu Trp Leu Phe Val Ala Ser Tyr Tyr Me
t Ala Tyr Phe Asn Ser
    290
    295
    300

Cys Leu Asn Ala Ile Ile Tyr Gly Leu Leu As
n Gln Asn Phe Arg Gln
305                         3
10                          3
15                          3
20

Glu Tyr Arg Lys Ile Ile Val Ser Leu Cys Th
r Thr Lys Met Phe Phe
            325
            330
            335

Val Asp Ser Ser Asn His Val Ala Asp Arg Il
e Lys Arg Lys Pro Ser
        340
        345
        350

Pro Leu Ile Ala Asn His Asn Leu Ile Lys Va
l Asp Ser Val
        355
        360
        365

(2) INFORMATION FOR SEQ ID NO:8:

(i) SEQUENCE CHARACTERISTICS:
        (A) LENGTH: 257 amino
acids
        (B) TYPE: amino acid
        (C) STRANDEDNESS: single
        (D) TOPOLOGY: unknown (ii) MOLECULE TYPE: cDNA (iii) HYPOTHETICAL: NO
```

```
    (iv) ANTI-SENSE: NO (vi) ORIGINAL SOURCE:
         (A) ORGANISM: Bos taurus
         (G) CELL TYPE: Melanocyte (xi) SEQUENCE DESCRIPTION: SEQ ID NO:8:

Tyr Pro Leu Ala Leu Ala Ser Ile Val Asn Asp Gly Trp Ser Leu Ser
 1               5                  10                  15

Ser Leu His Cys Gln Leu Ser Gly Phe Leu Met Gly Leu Ser Val Ile
            20                  25                  30

Gly Ser Val Phe Asn Ile Thr Gly Ile Ala Ile Asn Arg Tyr Cys Cys
        35                  40                  45

Ile Cys His Ser Leu Arg Tyr Asn Lys Leu Tyr Ser Ser Thr Asn Ser
    50                  55                  60

Leu Cys Tyr Val Phe Leu Ile Trp Met Leu Thr Leu Val Ala Ile Val
65                  70                  75                  80

Pro Asn Leu Cys Val Gly Thr Leu Gln Tyr Asp Pro Arg Ile Tyr Ser
                85                  90                  95

Cys Thr Phe Thr Gln Ser Val Ser Ser Ala Tyr Thr Ile Ala Val Val
            100                 105                 110

Val Phe His Phe Ile Val Pro Met Leu Val Val Ile Phe Cys Tyr Leu
        115                 120                 125

Arg Ile Trp Ala Leu Val Leu Gln Val Arg Trp Arg Val Lys Pro Asp
    130                 135                 140

Asn Lys Pro Lys Leu Lys Pro Gln Asp Phe Arg Asn Phe Val Thr Met
145                 150                 155                 160

Phe Val Val Phe Val Leu Phe Ala Ile Cys Trp Ala Pro Leu Asn Phe
                165                 170                 175

Ile Gly Leu Val Val Ala Ser Glu Pro Ala Ser Met Ala Pro Arg Ile
```

```
                    180
                         185
                              190

Pro Glu Trp Leu Phe Val Ala Ser Tyr Tyr Me
t Gly Tyr Phe Asn Ser
            195
                 200
                      205

Cys Leu Asn Ala Ile Ile Tyr Gly Leu Leu As
n Gln Asn Phe Arg Gln
      210
           215
                220

Glu Tyr Arg Lys Ile Ile Val Ser Leu Cys Th
r Thr Lys Met Phe Phe
225                 2
30                     2
35                        2
40

Val Asp Ser Ser Asn His Val Ala His Arg Il
e Lys Arg Lys Pro Ser
                245
                     250
                          255

Pro (2) INFORMATION FOR SEQ ID NO:9:

(i) SEQUENCE CHARACTERISTICS:
        (A) LENGTH: 153 amino
acids
        (B) TYPE: amino acid
        (C) STRANDEDNESS: single
        (D) TOPOLOGY: unknown (ii) MOLECULE TYPE: cDNA (iii) HYPOTHETICAL: NO (iv) ANTI-SENSE: NO (vi) ORIGINAL SOURCE:
        (A) ORGANISM: Sus scrof
a
        (G) CELL TYPE: Melanocy
te (xi) SEQUENCE DESCRIPTION: SEQ ID NO:9:

Tyr Cys Tyr Ile Cys His Ser Leu Lys Tyr As
p Arg Trp Tyr Ser Asn
1                 5
                      10
                           15

Arg Asn Ser Leu Cys Cys Val Phe Leu Ile Cy
s Val Leu Thr Leu Val
           20
                25
                     30

Ala Ile Val Pro Asn Leu Cys Met Gly Thr Le
u Gln Tyr Asp Pro Arg
       35
            40
                 45

Ile Tyr Ser Cys Thr Phe Ala Gln Ser Val Se
r Ser Ala Tyr Thr Ile
     50
          55
               60

Ala Val Val Val Phe His Phe Leu Val Pro Me
```

```
t Val Ile Val Ile Phe
65
70
75
80

Arg Tyr Leu Arg Ile Trp Val Leu Val Leu Gl
n Ile Arg Trp Arg Ala
             85
             90
             95

Lys Pro Glu Asn Asn Pro Arg Leu Lys Pro Gl
n Asp Phe Arg Asn Phe
          100
          105
          110

Val Thr Met Phe Val Val Phe Val Leu Phe Al
a Ile Cys Trp Ala Pro
       115
       120
       125

Leu Asn Phe Ile Gly Leu Ala Val Ala Ser As
p Pro Ala Ser Met Ala
     130
     135
     140

Pro Arg Ile Pro Glu Trp Leu Phe Val
145                     1
50
```

(2) INFORMATION FOR SEQ ID NO:10:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Sus scrofa
        (F) TISSUE TYPE: Vascular cambium (xi) SEQUENCE DESCRIPTION: SEQ ID NO:10:

TATCAGCCCT CCATAGTCAC AT
              22

(2) INFORMATION FOR SEQ ID NO:11:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Sus scrof (F) TISSUE TYPE: Vascular cambium (xi) SEQUENCE DESCRIPTION: SEQ ID NO:11:

GAAATTGTTG TCCATGACCT TTAT

24

(2) INFORMATION FOR SEQ ID NO:12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Sus scrofa
        (F) TISSUE TYPE: Vascular cambium (xi) SEQUENCE DESCRIPTION: SEQ ID NO:12:

TTGAATGCAG TGAACTCTTG

20

(2) INFORMATION FOR SEQ ID NO:13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Sus scrofa
        (F) TISSUE TYPE: Vascular cambium (xi) SEQUENCE DESCRIPTION: SEQ ID NO:13:

AGTCAACCCA GTTCTTTCTT

20

(2) INFORMATION FOR SEQ ID NO:14:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Sus scrofa (xi) SEQUENCE DESCRIPTION: SEQ ID NO:14:

TTCCGAGTCA AAGAGAACTT CG
                22

(2) INFORMATION FOR SEQ ID NO:15:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Sus scrofa (xi) SEQUENCE DESCRIPTION: SEQ ID NO:15:

TCATAGTCCG TGTCGATGAT CC
                22

(2) INFORMATION FOR SEQ ID NO:16:

(i) SEQUENCE CHARACTERISTICS:
            (A) LENGTH: 20 base pairs
            (B) TYPE: nucleic acid
            (C) STRANDEDNESS: single
            (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Homo sapiens (viii) POSITION IN GENOME:
            (B) MAP POSITION: 874

(xi) SEQUENCE DESCRIPTION: SEQ ID NO:16:

GGCATGTCCA AGGAAGCTGT
   20

(2) INFORMATION FOR SEQ ID NO:17:

(i) SEQUENCE CHARACTERISTICS:
            (A) LENGTH: 21 base pairs
            (B) TYPE: nucleic acid
            (C) STRANDEDNESS: single
            (D) TOPOLOGY: linear

```
        (ii) MOLECULE TYPE: cDNA (iii) HYPOTHETICAL: NO (iv) ANTI-SENSE: NO (vi) ORIGINAL SOURCE:
             (A) ORGANISM: Homo sapiens (viii) POSITION IN GENOME:
             (B) MAP POSITION: 874

(xi) SEQUENCE DESCRIPTION: SEQ ID NO:17:

GTTCTCCAGC ATCTCTCGGA T

21

(2) INFORMATION FOR SEQ ID NO:18:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapiens (viii) POSITION IN GENOME:
             (B) MAP POSITION: 874

(xi) SEQUENCE DESCRIPTION: SEQ ID NO:18:

GAGCAAGATG GAATGGGTT

19

(2) INFORMATION FOR SEQ ID NO:19:

(i) SEQUENCE CHARACTERISTICS:
             (A) LENGTH: 19 base pairs
             (B) TYPE: nucleic acid
             (C) STRANDEDNESS: single
             (D) TOPOLOGY: linear (ii) MOLECULE TYPE: cDNA (iii) HYPOTHETICAL: NO (iv) ANTI-SENSE: NO (vi) ORIGINAL SOURCE:
             (A) ORGANISM: Homo sapiens (viii) POSITION IN GENOME:
             (B) MAP POSITION: 874

(xi) SEQUENCE DESCRIPTION: SEQ ID NO:19:

CTCGGTGTCT GTAAAGGTG

19
```

(2) INFORMATION FOR SEQ ID NO:20:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: Exon II (xi) SEQUENCE DESCRIPTION: SEQ ID NO:20:

ATNACNGGNA TNGCNATHAA YMGNTA 26

(2) INFORMATION FOR SEQ ID NO:21:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Homo sapiens (viii) POSITION IN GENOME:
        (A) CHROMOSOME/SEGMENT: Exon II (xi) SEQUENCE DESCRIPTION: SEQ ID NO:21:

TTNARRCANS WRTTRTANGC CAT 23

(2) INFORMATION FOR SEQ ID NO:22:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Ovis ammon aries
        (G) CELL TYPE: Melanocy te (xi) SEQUENCE DESCRIPTION: SEQ ID NO:22:

TATTGCTACA TCTGACACAG TC

22

(2) INFORMATION FOR SEQ ID NO:23:

(i) SEQUENCE CHARACTERISTICS:
        (A) LENGTH: 22 base
pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Ovis ammo
n aries
        (G) CELL TYPE: Melanocy
te (xi) SEQUENCE DESCRIPTION: SEQ ID NO:23:

GCCACAAACA GCCACTCTGG GA

22

(2) INFORMATION FOR SEQ ID NO:24:

(i) SEQUENCE CHARACTERISTICS:
        (A) LENGTH: 20 base
pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Ovis ammo
n aries (viii) POSITION IN GENOME:
        (A) CHROMOSOME/SEGMENT: MT
NR1A (xi) SEQUENCE DESCRIPTION: SEQ ID NO:24:

TGTGTTTGTG GTGAGCCTGG

20

(2) INFORMATION FOR SEQ ID NO:25:

(i) SEQUENCE CHARACTERISTICS:
        (A) LENGTH: 20 base
pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO

```
    (iv) ANTI-SENSE: NO (vi) ORIGINAL SOURCE:
         (A) ORGANISM: Ovis ammo
n aries (viii) POSITION IN GENOME:
         (A) CHROMOSOME/SEGMENT: MT
NR1A (xi) SEQUENCE DESCRIPTION: SEQ ID NO:25:

ATGGAGAGGG TTTGCGTTTA

20
```